(12) United States Patent
Chiang et al.

(10) Patent No.: US 7,828,771 B2
(45) Date of Patent: Nov. 9, 2010

(54) SYSTEMS AND METHODS FOR DELIVERING DRUGS

(75) Inventors: Yet-Ming Chiang, Framingham, MA (US); Michael J. Cima, Winchester, MA (US); J. Richard Gyory, Sudbury, MA (US); Glenn R. Booma, Natick, MA (US)

(73) Assignee: Entra Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 12/181,085

(22) Filed: Jul. 28, 2008

(65) Prior Publication Data

US 2009/0028824 A1 Jan. 29, 2009

Related U.S. Application Data

(60) Provisional application No. 60/952,217, filed on Jul. 26, 2007, provisional application No. 60/989,605, filed on Nov. 21, 2007.

(51) Int. Cl.
*A61M 5/20* (2006.01)
(52) U.S. Cl. .................. 604/132; 604/153
(58) Field of Classification Search ............ 604/67, 604/132, 133, 151; 417/87.5
See application file for complete search history.

(56) References Cited

U.S. PATENT DOCUMENTS

| | | | |
|---|---|---|---|
| 5,016,047 A | 5/1991 | Meacham | |
| 5,800,420 A | 9/1998 | Gross et al. | |
| 5,848,911 A * | 12/1998 | Garcin | 439/395 |
| 5,858,001 A | 1/1999 | Tsals et al. | |
| 5,957,895 A | 9/1999 | Sage et al. | |
| 5,989,423 A | 11/1999 | Kamen et al. | |
| 6,530,900 B1 * | 3/2003 | Garcin et al. | 604/132 |
| 6,589,229 B1 * | 7/2003 | Connelly et al. | 604/890.1 |
| 6,682,500 B2 * | 1/2004 | Soltanpour et al. | 604/9 |
| 6,687,536 B1 * | 2/2004 | Beck et al. | 604/20 |
| 6,689,100 B2 | 2/2004 | Connelly et al. | |
| 6,699,218 B2 | 3/2004 | Flaherty et al. | |
| 6,752,787 B1 | 6/2004 | Causey, III et al. | |
| 6,960,192 B1 | 11/2005 | Flaherty et al. | |
| 7,005,078 B2 | 2/2006 | Van Lintel et al. | |
| 7,014,625 B2 | 3/2006 | Bengtsson | |
| 7,025,743 B2 | 4/2006 | Mann et al. | |

(Continued)

FOREIGN PATENT DOCUMENTS

DE 19809483 A1 9/1999

(Continued)

OTHER PUBLICATIONS

Osborne, Randall, Valeritas' Insulin Patch Takes Aim At Type II Drug Resisters, BioWorld Financial Watch, Sep. 4, 2006, vol. 14, No. 36, Atlanta, Georgia.

(Continued)

*Primary Examiner*—Nicholas D Lucchesi
*Assistant Examiner*—Gerald Landry, II
(74) *Attorney, Agent, or Firm*—Cooley LLP

(57) ABSTRACT

A patch pump device generally includes at least one fluid source, a fluid communicator, and an electrochemical actuator. The fluid communicator is in fluid communication with the fluid source. The electrochemical actuator is operative to cause fluid to be delivered from the fluid source into the fluid communicator.

52 Claims, 8 Drawing Sheets

U.S. PATENT DOCUMENTS

| | | |
|---|---|---|
| 7,044,928 B2 | 5/2006 | LeMay et al. |
| 7,115,108 B2 | 10/2006 | Wilkinson et al. |
| 7,144,384 B2 | 12/2006 | Gorman et al. |
| 7,156,838 B2 | 1/2007 | Gabel et al. |
| 7,273,889 B2 | 9/2007 | Memelstein et al. |
| 7,410,476 B2 | 8/2008 | Wilkinson et al. |
| 7,569,050 B2 | 8/2009 | Moberg et al. |
| D602,155 S | 10/2009 | Foley et al. |
| D602,586 S | 10/2009 | Foley et al. |
| 7,632,247 B2 | 12/2009 | Adams |
| 2001/0053887 A1* | 12/2001 | Douglas et al. ............ 604/152 |
| 2003/0135159 A1* | 7/2003 | Daily et al. ................ 604/141 |
| 2003/0167035 A1* | 9/2003 | Flaherty et al. ............. 604/67 |
| 2005/0119618 A1 | 6/2005 | Gonnelli |
| 2006/0095014 A1 | 5/2006 | Ethelfield |
| 2006/0102455 A1 | 5/2006 | Chiang et al. |
| 2006/0206099 A1 | 9/2006 | Olsen |
| 2007/0021733 A1 | 1/2007 | Hansen et al. |
| 2007/0049865 A1 | 3/2007 | Radmer et al. |
| 2007/0112301 A1 | 5/2007 | Preuthun et al. |
| 2007/0282269 A1 | 12/2007 | Carter et al. |
| 2007/0287753 A1 | 12/2007 | Charney et al. |
| 2007/0299397 A1 | 12/2007 | Alferness et al. |
| 2007/0299398 A1 | 12/2007 | Alferness et al. |
| 2007/0299399 A1 | 12/2007 | Alferness et al. |
| 2007/0299400 A1 | 12/2007 | Alferness et al. |
| 2007/0299401 A1 | 12/2007 | Alferness et al. |
| 2007/0299408 A1 | 12/2007 | Alferness et al. |
| 2008/0009805 A1 | 1/2008 | Ethelfield |
| 2008/0015494 A1 | 1/2008 | Santini, Jr. et al. |
| 2008/0051710 A1 | 2/2008 | Moberg et al. |
| 2008/0058718 A1 | 3/2008 | Adams et al. |
| 2008/0157713 A1 | 7/2008 | Chiang et al. |
| 2008/0167620 A1 | 7/2008 | Adams et al. |
| 2008/0215006 A1 | 9/2008 | Thorkild |
| 2008/0255516 A1 | 10/2008 | Yodfat et al. |
| 2008/0257718 A1 | 10/2008 | Chiang et al. |
| 2008/0269687 A1 | 10/2008 | Chong et al. |
| 2008/0281270 A1 | 11/2008 | Cross et al. |
| 2008/0317615 A1 | 12/2008 | Banister |
| 2008/0319414 A1 | 12/2008 | Yodfat et al. |
| 2009/0014320 A1 | 1/2009 | Chiang et al. |
| 2009/0036867 A1 | 2/2009 | Glejboel et al. |
| 2009/0054866 A1 | 2/2009 | Teisen-Simony et al. |
| 2009/0062747 A1 | 3/2009 | Saul |
| 2009/0088693 A1 | 4/2009 | Carter |
| 2009/0088694 A1 | 4/2009 | Carter et al. |
| 2009/0088722 A1 | 4/2009 | Wojcik |
| 2009/0099521 A1 | 4/2009 | Gravesen et al. |
| 2009/0099522 A1 | 4/2009 | Kamen et al. |
| 2009/0124997 A1 | 5/2009 | Pettis et al. |
| 2009/0163855 A1* | 6/2009 | Shin et al. ................... 604/66 |
| 2009/0163874 A1 | 6/2009 | Krag et al. |
| 2009/0171324 A1 | 7/2009 | Chong et al. |
| 2009/0182277 A1 | 7/2009 | Carter |
| 2009/0192471 A1 | 7/2009 | Carter et al. |
| 2009/0198215 A1 | 8/2009 | Chong et al. |
| 2009/0326454 A1 | 12/2009 | Cross et al. |
| 2009/0326455 A1 | 12/2009 | Carter |
| 2009/0326472 A1 | 12/2009 | Carter et al. |
| 2010/0022992 A1 | 1/2010 | Genosar et al. |
| 2010/0063438 A1* | 3/2010 | Bengtsson ................... 604/66 |

FOREIGN PATENT DOCUMENTS

| | | |
|---|---|---|
| EP | 2015806 B1 | 9/2009 |
| WO | 2004067066 A1 | 8/2004 |
| WO | 2005124918 A2 | 12/2005 |
| WO | 2006123329 A3 | 11/2006 |
| WO | 2007010522 A1 | 1/2007 |
| WO | 2007111880 A2 | 10/2007 |
| WO | 2007129317 A1 | 11/2007 |
| WO | 2008003122 A2 | 3/2008 |
| WO | 2008129549 A1 | 10/2008 |
| WO | WO 2008/129549 A1 | 10/2008 |

OTHER PUBLICATIONS

Codman 3000, Johnson & Johnson Company.
BioValue Products, e-Patch, Jun. 26, 2006, http://www.valeritas.com/epatch.shtml.

* cited by examiner (a)

(b)

(c)

(d)

SYSTEMS AND METHODS FOR DELIVERING DRUGS

CROSS-REFERENCE TO RELATED APPLICATIONS

This application claims the benefit of U.S. Provisional Application Ser. No. 60/952,217, filed Jul. 26, 2007. This application also claims the benefit of U.S. Provisional Application Ser. No. 60/989,605, filed Nov. 21, 2007. Both of these applications are incorporated herein by reference.

BACKGROUND OF THE INVENTION

This invention is generally in the field of medical devices, and more particularly in the field of drug delivery devices.

Drug delivery involves delivering a drug or other therapeutic compound into the body. Typically, the drug is delivered via a technology that is carefully selected based on a number of factors. These factors include but are not limited to the characteristics of the drug, such as drug dose, pharmacokinetics, complexity, cost, and absorption, the characteristics of the desired drug delivery profile (such as uniform, non-uniform, or patient-controlled), the characteristics of the administration mode (such as the ease, cost, complexity, and effectiveness of the administration mode for the patient, physician, nurse, or other caregiver), or other factors or combinations of these factors.

Conventional drug delivery technologies present various challenges. Oral administration of a dosage form is a relatively simple delivery mode, but some drugs may not achieve the desired bioavailability and/or may cause undesirable side effects if administered orally. Further, the delay from time of administration to time of efficacy associated with oral delivery may be undesirable depending on the therapeutic need. While parenteral administration by injection may avoid some of the problems associated with oral administration, such as providing relatively quick delivery of the drug to the desired location, conventional injections may be inconvenient, difficult to self-administer, and painful or unpleasant for the patient. Furthermore, injection may not be suitable for achieving certain delivery/release profiles, particularly over a sustained period of time.

Passive transdermal technology, such as a conventional transdermal patch, may be relatively convenient for the user and may permit relatively uniform drug release over time. However, some drugs, such as highly charged or polar drugs, peptides, proteins and other large molecule active agents, may not penetrate the stratum corneum for effective delivery. Furthermore, a relatively long start-up time may be required before the drug takes effect. Thereafter, the drug release may be relatively continuous, which may be undesirable in some cases. Also, a substantial portion of the drug payload may be undeliverable and may remain in the patch once the patch is removed.

Active transdermal systems, including iontophoresis, sonophoresis, and poration technology, may be expensive and may yield unpredictable results. Only some drug formulations, such as aqueous stable compounds, are suited for active transdermal delivery. Further, modulating or controlling the delivery of drugs using such systems may not be possible without using complex systems.

Infusion pump systems may be large and may require tubing between the pump and the infusion set, impacting quality of life. Further, infusion pumps may be expensive and may not be disposable. From the above, it would be desirable to provide new and improved drug delivery systems and methods that overcome some or all of these and other drawbacks.

SUMMARY OF THE INVENTION

A patch pump device generally includes at least one fluid source, a fluid communicator, and at least one electrochemical actuator. The fluid communicator is in fluid communication with the fluid source. The electrochemical actuator is operative to cause fluid to be delivered from the fluid source into the fluid communicator.

BRIEF DESCRIPTION OF THE DRAWINGS

FIG. 2 is a schematic view of an embodiment of an electrochemical actuator, wherein FIG. 2(a) illustrates the electrochemical actuator in a charged state and FIG. 2(b) illustrates the electrochemical actuator as it discharges.

FIG. 3 is a schematic view of another embodiment of an electrochemical actuator, wherein FIG. 3(a) illustrates the electrochemical actuator in a charged state and FIG. 3(b) illustrates the electrochemical actuator as it discharges.

FIG. 4 is a side cross-sectional view of an embodiment of a pump device, wherein FIG. 4(a) illustrates the pump device in an unassembled position; FIG. 4(b) illustrates the pump device in an assembled position; and FIG. 4(c) illustrates the pump device pumping fluid therefrom.

FIG. 5 illustrates another embodiment of a pump device, wherein FIG. 5(a) is a top plan view of the pump device in an unassembled position; FIG. 5(b) is a side cross-sectional view of the pump device in the unassembled position; FIG. 5(c) is a top plan view of the pump device in an assembled position; and FIG. 5(d) is a side cross-sectional view of the pump device in the assembled position.

FIG. 6 is a side cross-sectional view of another embodiment of a pump device, wherein FIG. 6(a) illustrates a needle insertion mechanism being attached to a base portion of the pump device; FIG. 6(b) illustrates the needle insertion mechanism inserting a needle and cannula through the base portion of the pump device; FIG. 6(c) illustrates the pump device in an unassembled position; and FIG. 6(d) illustrates the pump device in an assembled position.

FIG. 7 is a side cross-sectional view of another embodiment of a pump device, wherein FIG. 7(a) illustrates the pump device in an unassembled position and FIG. 7(b) illustrates the pump device in an assembled position.

FIG. 8 is a side cross-sectional view of another embodiment of a pump device, wherein FIG. 8(a) illustrates the pump device in an unassembled position and FIG. 8(b) illustrates the pump device in an assembled position.

DETAILED DESCRIPTION OF THE INVENTION

Described below are embodiments of systems and methods of delivering a fluid, which may include a drug, into a patient in need thereof. The patient may be a human or other mammal for example. In embodiments, the systems and methods may embody a pump device suited for subcutaneous or intravenous delivery of a fluid, which may or may not include one or more drugs. The pump device may employ an electrochemical actuator, which may have characteristics of both a battery and a pump. Specifically, the electrochemical actuator may include an electrochemical cell that produces a pumping force as the cell discharges. Thus, the pump device may have relatively fewer parts than a conventional drug pump, such that the pump device is relatively more compact, disposable, and reliable than conventional drug pumps. These attributes of the pump device may permit reducing the cost and the discomfort associated with infusion drug therapy. Further, such a pump device may have a control means, such as a controller and/or other circuitry, operative to regulate drug or fluid flow from the pump device. Such control means may permit implementing one or more release profiles using the pump device, including release profiles that require uniform flow, non-uniform flow, continuous flow, discontinuous low, programmed flow, scheduled flow, user-initiated flow, or feedback responsive flow, among others. Thus, the pump device may effectively deliver a wider variety of drug therapies than other pump devices.

Figure 1:
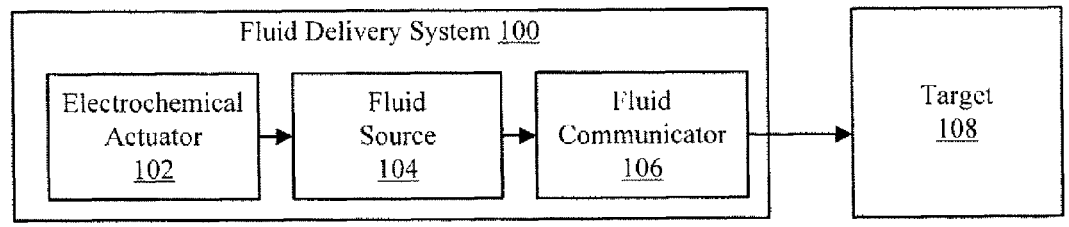
FIG. 1 is a schematic block diagram illustrating an embodiment of a fluid delivery system.

FIG. 1 is a schematic block diagram illustrating an embodiment of a fluid delivery system 100. The fluid delivery system 100 generally includes an electrochemical actuator 102 associated with a fluid source 104 and a fluid communicator 106. The fluid source 104 may contain a fluid to be delivered into a target 108 via the fluid communicator 106. The electrochemical actuator 102 may actuate or otherwise create a pumping force to deliver the fluid from the fluid source 104 into the fluid communicator 106. Specifically, the electrochemical actuator 102 may be any device that experiences a change in volume or position in response to an electrochemical reaction that occurs therein. For example, the electrochemical actuator 102 may include a charged electrochemical cell, and at least a portion of the electrochemical cell may actuate as the electrochemical cell discharges. Thus, the electrochemical actuator 102 may be considered a self-powered actuator or a combination battery and actuator.

In use, the fluid communicator 106 may be associated with the target 108, and the electrochemical actuator 102 may be operated. Specifically, the electrochemical actuator 102 may discharge and actuate. The resulting mechanical work may act on the fluid source 104 or may be transferred through intervening mechanics to the fluid source 104, causing the fluid to be delivered through the fluid communicator 106 into the target 108.

In embodiments, the fluid delivery system 100 may be a system for delivering a drug into a human body. In such embodiments, the fluid source 104 may be a reservoir, pouch, or bladder, or other known fluid source containing a drug in fluid form, and the target 108 may be a human in need of a drug therapy or prophylaxis. The fluid communicator 106 may be a needle, catheter, cannula, infusion set, or other known delivery device that is inserted into or otherwise associated with the human body for drug delivery. When the electrochemical reaction is occurring in the electrochemical actuator 102, the electrochemical actuator 102 may cause the drug to be communicated from the fluid source 104 into the human body. Such drug delivery may be subcutaneous, intravenous, intraarterial, intramuscular, intracardiac, intraosseous, intradermal, intrathecal, intraperitoneal, intratumoral, epidural, and/or peri-neural depending on, for example, the location of the fluid communicator 106 and/or the entry location of the drug.

In embodiments, the fluid delivery system 100 may be used to deliver a drug formulation which comprises a drug, meaning a therapeutic or prophylactic agent including an active pharmaceutical ingredient. In other embodiments, the fluid delivery system 100 may deliver a fluid that does not contain a drug. For instance, the fluid may be a saline solution or a diagnostic agent, such as a contrast agent.

The drug may be in a pure form or formulated in a solution, a suspension, or an emulsion, among others, using one or more pharmaceutically acceptable excipients known in the art. For example, a pharmaceutically acceptable vehicle for the drug may be provided, which may be essentially any aqueous or non-aqueous vehicle known in the art. Examples of aqueous vehicles include physiological saline solutions, solutions of sugars such as dextrose or mannitol, and pharmaceutically acceptable buffered solutions, and examples of non-aqueous vehicles include fixed vegetable oils, glycerin, polyethylene glycols, alcohols, and ethyl oleate. The vehicle may further include antibacterial preservatives, antioxidants, tonicity agents, buffers, stabilizers, or other components.

Representative examples of drugs that may be delivered with embodiments of the present device include, but are not limited to, opioid narcotics such as fentanyl, remifentanyl, sufentanil, morphine, hydromorphone, oxycodiene and salts thereof; NonSteroidal Antinflamatories (NSAIDs) such as diclofenac, naproxen, ibuprofin, and celecoxib; local anesthetics such as lidocaine, tetracaine, and bupivicaine; dopamine antagonists such as apomorphine, rotigotine, and ropinerole; drugs used for the treatment and/or prevention of allergies such as antihistamines, antileukotrienes, anticholinergics, and immunotherapeutic agents; antispastics such as tizanidine and baclofin; vitamins such as niacin; Selegiline; and rasagiline. Essentially any peptide, protein, biologic, or oligonucleotide, among others, that is normally delivered by subcutaneous, intramuscular, or intravenous injection or other parenteral routes, may be delivered using embodiments of the devices described herein. In embodiments, the device may be used to administer a drug combination of two or more different drugs using a single or multiple delivery port and being able to deliver the agents at a fixed ratio or by means enabling the delivery of each agent to be independently modulated. For example, two or more drugs can be administered simultaneously or serially, or a combination (e.g. overlapping) thereof.

Although the fluid delivery system 100 and other systems and methods described herein are generally described as communicating drugs into a human body, such systems and methods may be employed to deliver any fluid of any suitable biocompatibility or viscosity into any object, living or inanimate. For example, the systems and methods may be employed to deliver other biocompatible fluids into living beings, including human beings and other animals. Further, the systems and methods may deliver drugs or other fluids into living beings other than human beings, such as animals and plant life. Also, the systems and methods may deliver any fluids into any target, living or inanimate. The systems and methods described herein are generally systems and methods of delivering fluids using an electrochemical actuator, including a self-powered actuator and/or combined battery and actuator.

Embodiments of such electrochemical actuators are generally described in U.S. patent application Ser. No. 11/150,477 entitled "Electrochemical Methods, Devices, and Structures" by Chiang et al., U.S. patent application Ser. No. 11/881,830 entitled "Electrochemical Actuator" by Chiang et al., and U.S. patent application Ser. No. 12/035,406 entitled "Electrochemical Actuator" by Chiang et al., each of which is herein incorporated by reference. Such electrochemical actuators may include at least one component that responds to the application of a voltage or current by experiencing a change in volume or position. The change in volume or position may produce mechanical work that may act on a fluid source or may be transferred to a fluid source, such that a fluid can be delivered out of the fluid source.

In embodiments, the electrochemical actuator may include a positive electrode and a negative electrode, at least one of which is an actuating electrode. These and other components of the electrochemical actuator may form an electrochemical cell, which may initially be charged. The electrochemical cell may begin discharging when a circuit between the electrodes is closed, causing the actuating electrode to actuate. The actuating electrode may thereby perform work upon another structure, such as the fluid source or transfer structure associated with the fluid source. The work may cause fluid to be pumped or otherwise dispensed from the fluid source into the target.

More specifically, the actuating electrode may experience a change in volume or position when the closed circuit is formed, and this change in volume of position may perform work upon the fluid source or transferring structure. For example, the actuating electrode may expand, bend, buckle, fold, cup, elongate, contract, or otherwise experience a change in volume, size, shape, orientation, arrangement, or location, such that at least a portion of the actuating electrode experiences a change in volume or position. In embodiments, the change in volume or position may be experienced by a portion of the actuating electrode, while the actuating electrode as a whole may experience a contrary change or no change whatsoever. It is noted that the electrochemical actuator may actually include a number of electrochemical actuators arranged in series, parallel, or some combination thereof. For example, a number of such electrochemical actuators may be stacked together. As another example, concurrent or sequenced delivery of multiple agents may be achieved by including one or more electrochemical actuators acting on two or more fluid sources.

Figure 2:
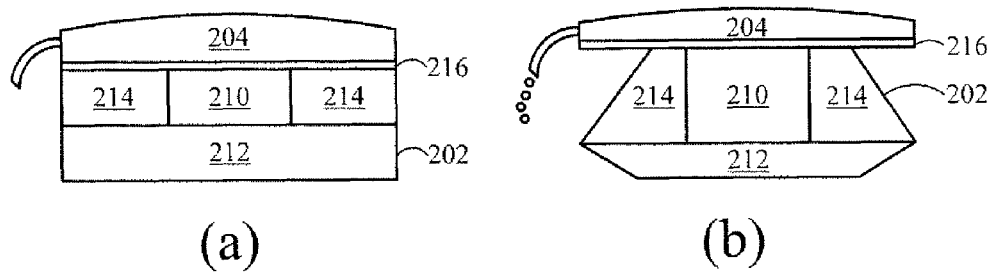

FIG. 2 is a schematic of an embodiment of an electrochemical actuator 202. As shown, the electrochemical actuator 202 may include a positive electrode 210, a negative electrode 212, and an electrolyte 214. These components may form an electrochemical cell that is initially discharged and is then charged before use, or is initially charged, as shown in FIG. 2(a). The positive electrode 210 may be configured to expand in the presence of the electrolyte 214. When a circuit between the electrodes 210, 212 is closed, current may travel from the positive electrode 210 to the negative electrode 212. The positive electrode 210 may experience a change in volume, resulting in longitudinal displacement of at least a portion of the positive electrode 210, as shown in FIG. 2(b). Thereby, the positive electrode 210 may exert a pumping force or pressure on a fluid reservoir 204 or associated transfer structure 216, such as the illustrated plate. The pumping force or pressure may cause fluid to be pumped from the fluid reservoir 204. Thus, the electrochemical actuator 202 may be considered a self-powered electrochemical pump. In the illustrated embodiment, the electrochemical cell has a positive electrode 210 selected to have a lower chemical potential for the working ion when the cell is charged, and is thereby able to spontaneously accept working ions from the negative electrode 212 as the cell is discharged. In embodiments the working ion includes but is not limited to the proton or lithium ion. When the working ion is lithium, the positive electrode 210 may comprise one or more lithium metal oxides including $LiCoO_2$, $LiFePO_4$, $LiNiO_2$, $LiMn_2O_4$, $LiMnO_2$, $LiMnPO_4$, $Li_4Ti_5O_{12}$, and their modified compositions and solid solutions; oxide compound comprising one or more of titanium oxide, manganese oxide, vanadium oxide, tin oxide, antimony oxide, cobalt oxide, nickel oxide or iron oxide; metal sulfides comprising one or more of $TiS_2$, $MoS_2$, $WS_2$, and their modified compositions and solid solutions; a metal, metal alloy, or intermetallic compound comprising one or more of aluminum, silver, gold, boron, bismuth, gallium, germanium, indium, lead, antimony, silicon, tin, or zinc; a lithium-metal alloy; or carbon comprising one or more of graphite, a carbon fiber structure, a glassy carbon structure, a highly oriented pyrolytic graphite, or a disordered carbon structure. The negative electrode 212 may comprise lithium metal, a lithium metal alloy, or any of the preceding compounds listed as positive electrode compounds, provided that such compounds when used as a negative electrode are paired with a positive electrode that is able to spontaneously accept lithium from the negative electrode when the cell is charged. Other configurations are also possible.

In embodiments, the electrochemical actuator may include an anode, a cathode, and a species, such as a lithium ion. At least one of the electrodes may be an actuating electrode that includes a first portion and a second portion. The portions may have at least one differing characteristic, such that in the presence of a voltage or current, the first portion responds to the species in a different manner than the second portion. For example, the portions may be formed from different materials, or the portions may differ in thickness, dimension, porosity, density, or surface structure, among others. The electrodes may be charged, and when the circuit is closed, current may travel. The species may, intercalate, de-intercalate, alloy with, oxide, reduce, or plate with the first portion to a different extent than the second portion. Due to the first portion responding differently to the species than the second portion, the actuating electrode may experience the change in volume or position.

Figure 3:
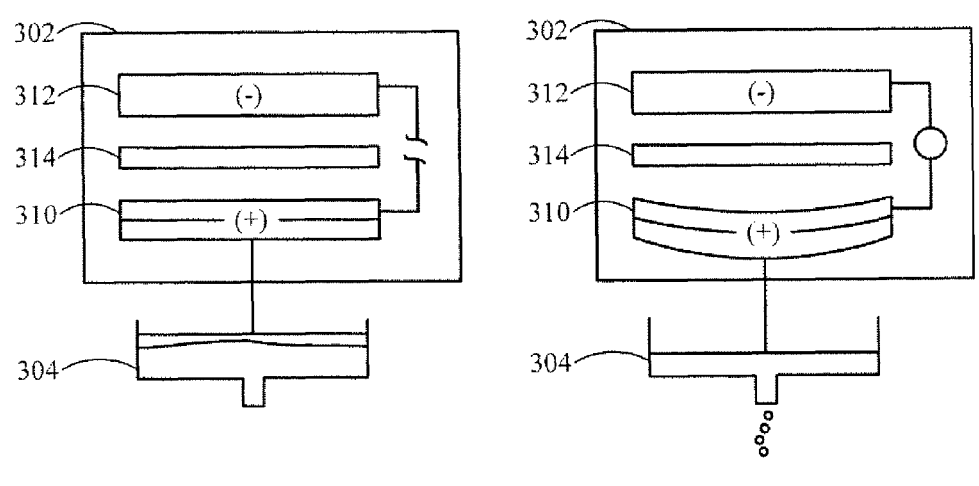

An example of such an embodiment is shown in FIG. 3, which is a schematic view of another embodiment of an electrochemical actuator 302. The electrochemical actuator 302 may include a positive electrode 310, a negative electrode 312, and a species 314. The species 314 may be an electrolyte that includes, for example, a lithium ion. The positive electrode 310 may include a first portion and a second portion. The first portion may include a material that is dimensionally active when in the presence of species. For example, aluminum expands upon alloying with or being intercalated by lithium. The second portion may include a material that is not dimensionally active when in the presence of the species, or is relatively less dimensionally active than the material of the first portion. For example, copper does not substantially intercalate or alloy with lithium. Thus, the positive electrode 310 may be considered a bimorph structure, with one of the portions serving as a positive current collector.

The negative electrode 312 may serve as a negative current collector. For example, the negative electrode 312 may include a layer of lithium metal bonded to or deposited on a layer of copper. Initially, the electrodes may be charged but may not form a closed circuit, as shown in FIG. 3(a). The positive electrode 310 may have a lower chemical potential for lithium than the negative electrode 312. When the circuit between the two electrodes is closed, as shown in FIG. 3(b), current may flow toward the negative electrode 312. The first portion of the positive electrode 310 may alloy or intercalate with the lithium, causing an expansion in volume, while the second portion may act as a mechanical constraint. Thereby, the positive electrode 310 may bend or otherwise displace. The displacement of the positive electrode 310 may be transferred to a fluid reservoir 304, causing the fluid reservoir 304 to expel fluid.

As mentioned above, such an electrochemical actuator may power a fluid delivery device suited delivering of a drug-containing or non-drug containing fluid into a human patient or other target. Such a fluid delivery system may be embodied in a relatively small, self-contained, and disposable device, such as a patch device that can be removably attached to the skin of the human body. The patch device may be relatively small and self-contained because the electrochemical actuator serves as both the battery and a pump. The small and self-contained nature of the device advantageously may permit concealing the device beneath clothing and may allow the patient to continue normal activity as the drug is delivered. External tubing may not be required to communicate fluid from the fluid reservoir into the body, unlike conventional drug pumps. Instead, any tubing may be contained within the device, and a needle or other fluid communicator may extend from the device into the body. The electrochemical actuator may initially be charged, and may begin discharging once the patch device is activated to pump or otherwise deliver the drug or other fluid into the body. Once the electrochemical actuator has completely discharged or the fluid reservoir is empty, the patch device may be removed and discarded. The small and inexpensive nature of the electrochemical actuator and other components of the device may permit disposing of the entire device, unlike conventional pump devices having a pump that is retained. Thus, the device may permit drug delivery, such as subcutaneous or intravenous drug delivery, over a time period that may vary from several minutes to several days. Subsequently, the device may be removed from the body and discarded.

For the purposes of this disclosure, the term "disposable" generally means a single use device, or a component thereof, that is intended to be discarded. Because the electrochemical actuator may serve as a battery, the electrochemical actuator may discharge with use, and thereafter may be discarded. Because the electrochemical actuator also serves as the pumping mechanism, however, discarding the electrochemical actuator also discards the pumping mechanism. Such a configuration differs from a conventional infusion pump, which includes a pumping mechanism that is retained for subsequent reuse. Unlike a conventional infusion pump, a patch pump device comprising the electrochemical actuator may be completely disposable.

Such a device may generally include a drug or fluid delivery system associated with a housing. As generally described above, the drug delivery system may include an electrochemical actuator suited to drive a drug from a fluid reservoir through a needle or other fluid communicator. The housing may at least partially contain the fluid delivery system and may be suit for removably associating the fluid delivery system with human skin.

So that the device can be worn on the skin, a releasable adhesive may at least partially coat an underside of the housing. The adhesive may be non-toxic, biocompatible, and releasable from human skin. To protect the adhesive until the device is ready for use, a removable protective covering may cover the adhesive, in which case the covering may be removed before the device is applied to the skin. Alternatively, the adhesive may be heat or pressure sensitive, in which case the adhesive may be activated once the device is applied to the skin. Example adhesives include but are not limited to acrylate based medical adhesives of the type commonly used to affix medical devices such as bandages to skin. However, the adhesive is not necessary and may be omitted, in which case the housing may be associated with the skin, or generally with the body, in any other manner.

The size, shape, and weight of the device may be selected so that the device may be comfortably worn on the skin after the device is applied via the adhesive. For example, the device may have a size in the range of about one inch by about one inch by about 0.1 inches to about five inches by about five inches by about one inch, and in some embodiments in a range of about two inches by about two inches by about 0.25 inches to about four inches by about four inches by about 0.67 inches. The weight of the device may be in the range of about five grams to about two hundred grams, and in some embodiments in a range of about fifteen grams to about one hundred grams. The device may be able to dispense a volume in the range of about 0.1 milliliters to about one thousand milliliters, and in some cases in the range of about 0.3 milliliters to about one hundred milliliters, such as between about 0.5 milliliters and about five milliliters. The shape of the device may be selected so that the device may be relatively imperceptible under clothing. For example, the housing may be relatively smooth and free from sharp edges. However, any size, shape, or weight is possible.

The housing may be formed from a material that is relatively lightweight and flexible, yet sturdy. The housing also be may formed from a combination of materials such as to provide specific portions that are rigid and specific portions that are flexible. The material may also be relatively low-cost, so that the device may be disposable. Example materials include plastic and rubber materials, such as polystyrene, polybutene, carbonate, urethane rubbers, butene rubbers, silicone, and other comparable materials and mixtures thereof, although a combination of these materials or any other material may be used.

In embodiments, the housing may include two portions: a base portion and a movable portion. The base portion may be suited for attaching to the skin. For example, the base portion may be relatively flexible. An adhesive may be deposited on an underside of the base portion, which may be relatively flat or shaped to mate with a particular body area. The movable portion may be sized and shaped for association with the base portion. In embodiments, the two portions may be designed to lock together, such as via a locking mechanism. In some cases, the two portions may releasably lock together, such as via a releasable locking mechanism, so that the movable portion may be removably associated with the base portion. To assemble the device, the movable portion may be movable with reference to the base portion between an unassembled position and an assembled position. In the assembled position, the two portions may form a device having an outer shape suited for concealing the device under clothing. Embodiments of such a device are generally described below with reference to FIGS. 4-10, although a range of configurations are possible.

Figure 4:
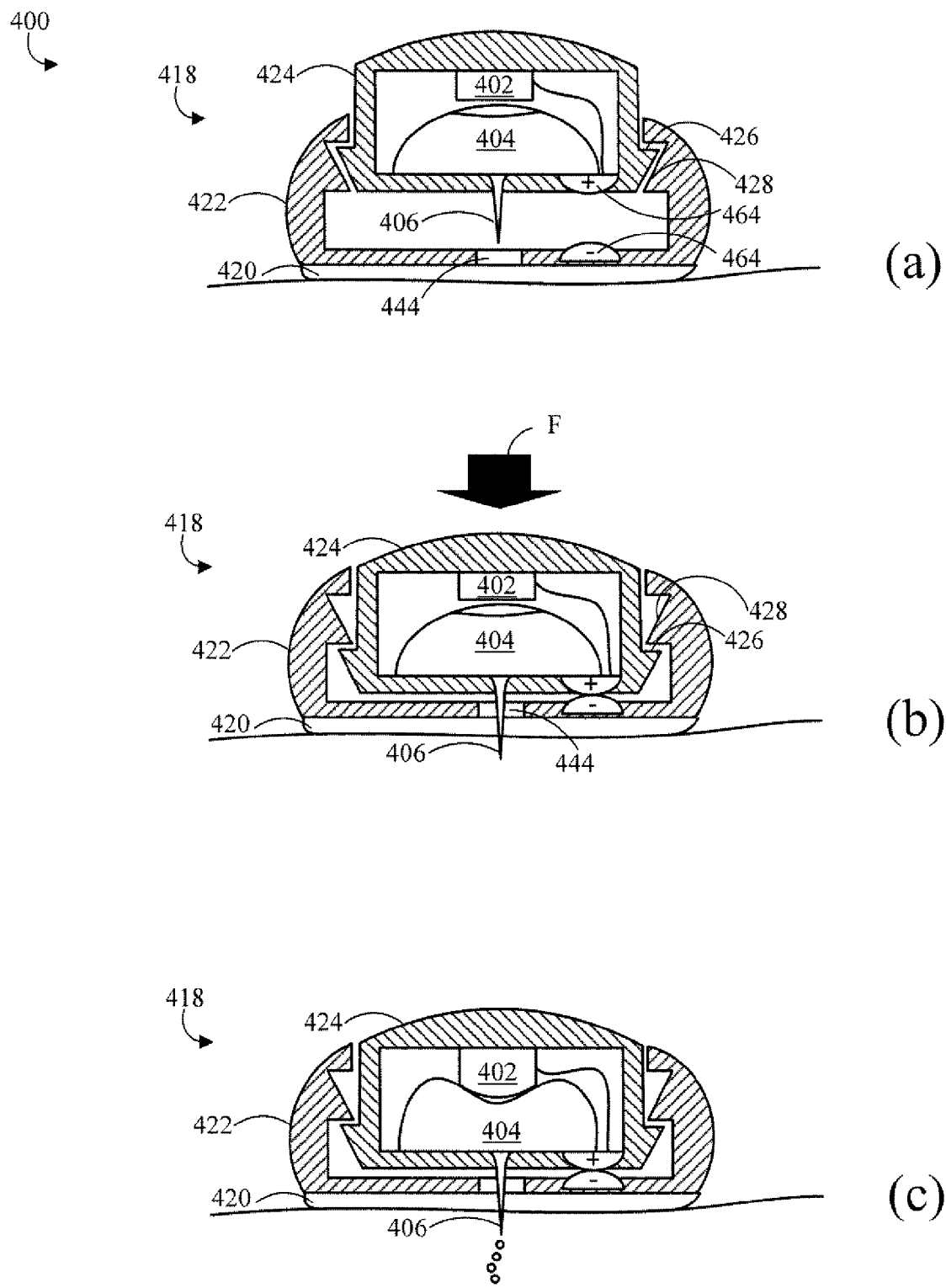

FIG. 4 is a side cross-sectional view of an embodiment of a patch device 400. The device 400 generally includes a fluid delivery system associated with a housing 418, which may include a base portion 422 and a movable portion 424. An adhesive 420 may be positioned on an underside of the base portion 422. The movable portion 424 may house one or more components of the fluid delivery system, such as an electrochemical actuator 402, a fluid reservoir 404, and fluid communicator 406. The movable portion 424 may be sized and shaped for insertion into the base portion 422. More specifically, the movable portion 424 may be movable with reference to the base portion 422 between an unassembled position shown in FIG. 4(a), and an assembled position shown in FIGS. 4(b-c). In the assembled position, the two portions 422, 424 may mate and lock together. When assembled, the outer surface of the device 400 may be relatively smooth and easy to conceal under clothing.

In the embodiment illustrated in FIG. 4, a releasable locking mechanism is formed by detents 426 located on an exterior surface of the movable portion 424 and a grooved flange 428 located on an interior surface of the base portion 422. In the unassembled position, the detents 426 rest in the grooved flange 428 to support the movable portion 424 above the base portion 422. To assemble the device 400, a force F is applied to the movable portion 424 to push it downward. The force F causes the grooved flange 428 to flex outward and the detent 426 to travel past the grooved flange 428. Thus, the movable portion 424 travels further into the base portion 422 and becomes firmly seated therein, The grooved flange 428 returns to prevent the detent 426 from moving upward, releasably locking the device 400 together. When so assembled, the device 400 takes on a bulbous shape that is relatively free from sharp edges. It is noted that, in some embodiments, the locking mechanism may not be releasable.

Figure 5:
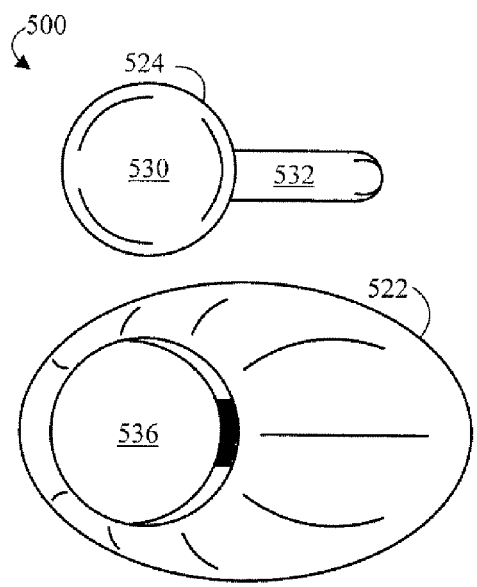
Figure 5:
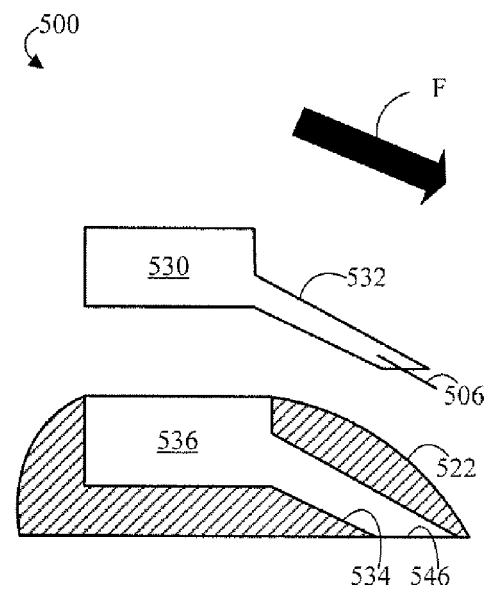
Figure 5:
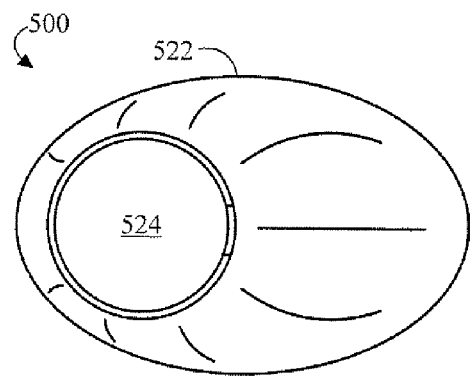
Figure 5:
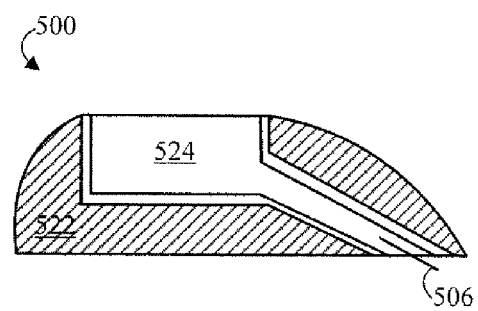

In the embodiment shown in FIG. 5, the device 500 generally includes a housing formed from a base portion 522 and a movable portion 524. Like the device 400, the base portion 522 may have an adhesive on an underside for associating the device 500 with the skin (not shown for clarity). A fluid delivery system may generally be contained in the movable portion 524 (not shown for clarity).

More specifically, the base portion 522 may have a relatively oval exterior and an interior that is sized and shaped to receive the movable portion 524. For example, the movable portion 524 may have a body 530 and a projection 532, and the base portion 522 may have an interior slot 534 and an opening 536. The interior slot 534 may be sized and shaped for receiving the projection 532, and the opening 536 may be sized and shaped for receiving the body 530. To assemble the device 500, the projection 532 may be inserted through the opening 536 along the slot 534, as shown in FIG. 5(b). The body 530 may be pressed into the opening 536 so that the movable portion 524 becomes firmly seated in the base portion 522, as shown in FIG. 5(d). When so assembled, the shape of the movable portion 524 may naturally limit its upward and rearward movement, releasably locking the two portions 522, 524 together. The assembled device 500 may take on a smooth oval shape that is relatively free from sharp edges and has a relatively low profile, so that the device 500 may be concealed under clothing.

Figure 6:
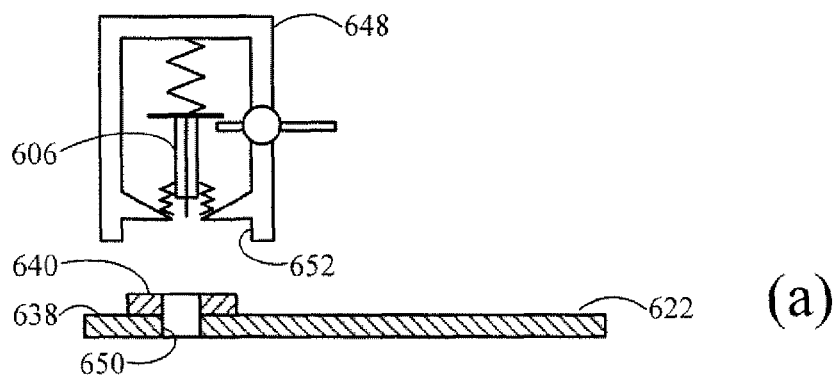
Figure 6:
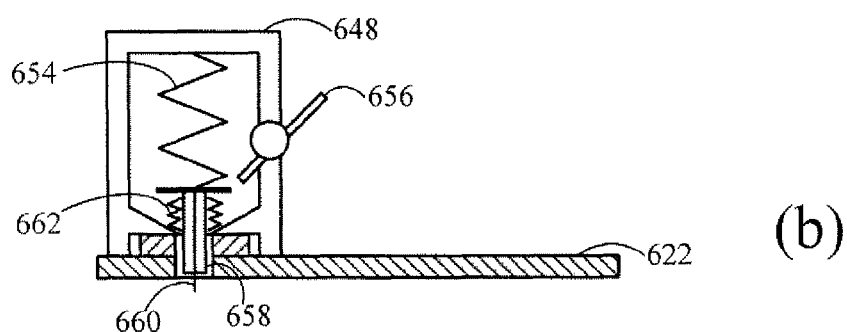
Figure 6:
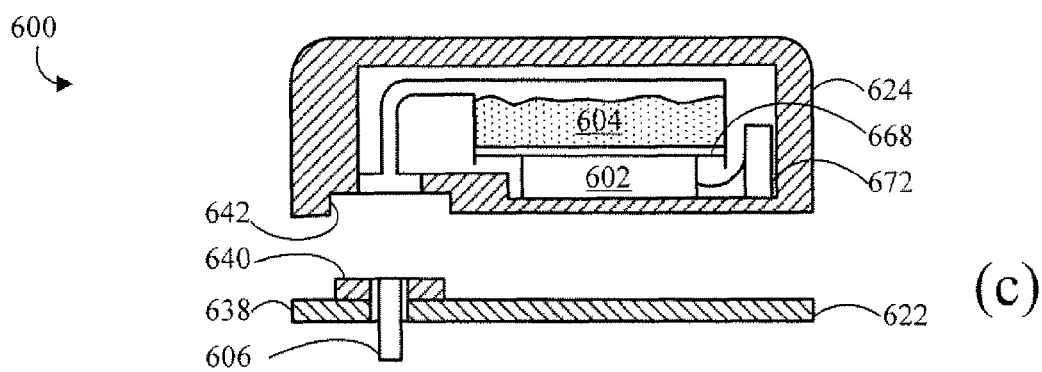
Figure 6:
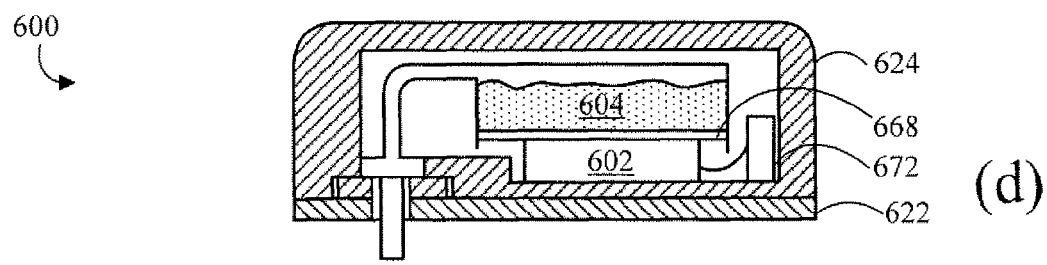

In the embodiment shown in FIG. 6, specifically FIG. 6(c) and FIG. 6(d), the device 600 may include a movable portion 624 that snaps onto an exterior of a base portion 622 instead of being inserted therein. Specifically, the base portion 622 may include a base 638 and a guide 640 that projects upward from the base 638. The base 638 may be a layer of adhesive, such as a flexible, double-sided layer of adhesive. Alternatively, the base 638 may comprise a plate having an adhesive on an underside. The movable portion 624 may have a cavity that houses components of the fluid delivery system, such as an electrochemical actuator 602, a fluid source 604, and associated electronics 672 (embodiments of which are described below with reference to FIG. 10). A recess 642 may be formed in the movable portion 624 for receiving the guide 640. To assemble the base portion 622 and the movable portion 624, the movable portion 624 may be positioned over the base portion 622 as shown in FIG. 6(c). The guide 640 may locate the recess 642, so that the portions 622, 624 are properly aligned. A force may be applied to press the movable portion 624 onto the base portion 622, as shown in FIG. 6(d). The guide 640 and the recess 642 may form a snap fitting, such that the device 600 becomes releasably locked together. Alternatively, the movable portion 624 may adhere to the base portion 622, such as in embodiments in which the base 638 is a double-side layer of adhesive. When assembled, the device 600 has a relatively smooth and low profile exterior that may permit concealing the device beneath clothing.

It should be noted that different embodiments of the device may be assembled using different hand motions. For example, the device 400 shown in FIG. 4 may be assembled by exerting a force on the movable portion 424 in a direction generally perpendicular to the surface of the skin, as shown in FIG. 4(b), while the device 500 shown in FIG. 5 may be assembled by exerting a force on the movable portion 524 in a direction that forms an angle with the surface of the skin, as shown in FIG. 5(b). Thus, different embodiments of the device may be better suited for assembly on different parts of the body or with fluid communicators inserted at different angles, as further described below. It also should be noted that some embodiments of the device, such as the device 400, the device 500, and the device 600 may be assembled using one hand. Assembling the device with one hand may facilitate attaching the device to a portion of the body that cannot be accessed easily. For example, some drugs or other fluids may be infused through the backside of the body, which may be difficult to access with both hands. Assembling the device on the backside of the body, for example, may be relatively easy with embodiments of the device that can be assembled using one hand.

In embodiments, the device may be designed such that assembling the device simultaneously inserts the fluid communicator into the body. Specifically, the fluid communicator may initially be retracted inside the housing and may be transferred from the housing into the body during assembly of the device. More specifically, the force that causes the housing to move from the unassembled position to the assembled position may also be effective to cause the needle to enter the body.

In the embodiment of the device 400 shown in FIG. 4, for example, the fluid communicator 406 may be a needle extending downward from the movable portion 424, When the device 400 is in the unassembled position, as shown in FIG. 4(a), the needle may be protected inside the base portion 422. A septum 444 or other penetrable member may be positioned in the base portion 422 adjacent to the needle, enclosing the base portion 422 so that the needle is not exposed to contaminants. When the force F is applied to move the movable portion 424 to the assembled position, as shown in FIG. 4(*b*), the needle penetrates the septum 444 and enters the skin. Because the force F is applied relatively perpendicular to the surface of the skin, the needle may enter the body at an angle that is relatively perpendicular to the surface of the skin. Such a configuration may be suited for patients that prefer inserting the needle in a perpendicular orientation, or for drugs or other fluids that are suited for being delivered via a needle in a perpendicular orientation. However, in other embodiments, other configurations are possible.

For example, in the embodiment of the device 500 shown in FIG. 5, the fluid communicator 506 may be a needle positioned at an end of the projection 532. The slot 534 may extend downward through the base portion 522, forming an angle with an underside of the base portion 522. The slot 534 may terminate in an aperture 546 formed through the underside of the base portion 522. The projection 532 may be sized such when the projection 532 is positioned in the slot 534, the needle passes through the aperture 546 into the skin. To assemble the device 500, the projection 532 is inserted through the slot 534. The force F is applied at an angle with reference to the surface of the skin to push the projection 532 along the slot 534, such that continued application of the force F inserts the needle into the body at an angle with reference to the surface of the skin. Inserting the needle at an angle may be preferred by some users and/or for some types of drug or fluid delivery.

In the embodiments described above with reference to FIG. 4 and FIG. 5, the force that causes the device to move into the assembled position is the same force that acts on the needle to insert the needle into the body. In such embodiments, the needle travels into the body in the same direction that the movable portion travels into the base portion. In other embodiments, the device may include mechanics that alter the direction of the force before the force acts on the needle. In such embodiments, the force may act on the movable portion in one direction and may act on the needle in another direction. For example, the mechanics may alter the direction of a perpendicular force before the force acts on the needle, so that the force can insert the needle into the body at an angle. Example mechanics may include a spring and a latch, wherein associating the movable portion with the base portion releases the latch to cause the spring to insert the needle into the body. In such embodiments, the mechanics may permit selecting the insertion angle of the needle, such as by rotating a dial or sliding a slider, so that the user can adjust the insertion angle based on his personal preference. A person of skill may be able to design such mechanics based on the disclosure above.

In still other embodiments, the force that causes the needle to enter the body may be applied completely separately from the force that places the device in the assembled position. For example, the needle may be manually inserted into the body before the device is associated with the needle. As another example, the electrochemical actuator may apply a force to the needle to insert the needle into the body. Further, a separate insertion mechanism may be provided for inserting the needle into the body.

Such an embodiment is shown in FIG. 6, specifically with reference to FIG. 6(*a*) and FIG. 6(*b*). Specifically, the device 600 may be suited for use with a separate needle insertion mechanism 648. The needle insertion mechanism 648 may be adapted for inserting a fluid communicator 606, such as a needle or cannula, through the base portion 622 of the device 600 and into the body. For example, the base portion 622 may include an opening 650 for receiving the fluid communicator 606, the opening 650 being formed through the guide 640 and the base plate 638. To permit aligning the needle insertion mechanism 648 with the base portion 622, and more specifically, to permit aligning the fluid communicator 606 with the opening 650, the needle insertion mechanism 648 may include a recess 652 sized and shaped to mate with the guide 640.

To insert the fluid communicator 606, the needle insertion mechanism 648 may be placed on the base portion 622, as shown in FIG. 6(*b*). A spring 654, which is generally retained within the needle insertion mechanism 648 in a compressed state, may be released via a releasable latch 656. The spring 654 may be in communication with the fluid communicator 606 and may expel the fluid communicator 606 out of the needle insertion mechanism 648 when the latch 656 is released. The fluid communicator 606 may travel through the opening 650, as shown in FIG. 6(*b*), and into the body, as shown in FIG. 6(*c*). Thereafter, the needle insertion mechanism 648 may be removed from the base portion 622, as shown in FIG. 6(*c*), so that the movable portion 624 may be positioned thereon as shown in FIG. 6(*d*). The needle insertion mechanism 648 may subsequently be discarded, or may be saved for re-use depending on the embodiment.

In embodiments, the fluid communicator 606 may be a soft cannula 658. A needle 660 may be fixedly associated with the spring 654 to initially pierce the skin and assist in inserting the soft cannula 658 into the body, as shown in FIG. 6(*b*). The needle 660 may subsequently be retracted or removed from the body, leaving the soft cannula 658 in place, as shown in FIG. 6(*c*). An aligning guide 662 may further guide the soft cannula 658 into the body, although the aligning guide 662 is not necessary and may be omitted.

In embodiments, the needle insertion mechanism may be designed for one handed operation to facilitate inserting the catheter in hard to reach places. Further, the needle insertion mechanism may be designed to insert the needle at a variety of different angles, including a user-selected angle. Fluid communicators other than needles or soft cannulas may be inserted by the needle insertion mechanism, depending on the embodiment. The needle inserting force may be supplied by the spring or in other manners, such as by the user, manually, in which case the spring may be omitted. Although the illustrated needle insertion mechanism is separate from the device, which permits reducing the size and/or weight of the device, the needle insertion mechanism may be an integral part of the device that is retained within the device after the needle is inserted. It also should be noted that the configuration described above, in which a piercing needle that assists with inserting a soft cannula is subsequently removed from the body, may be employed with reference to other embodiments.

By way of example, the fluid communicator is described above as being a needle or a cannula. In embodiments, the needle or a soft cannula may be relatively small for comfort. In other embodiments, the fluid communicator can be any catheter or other device for delivering fluids into the body, or combinations thereof. In embodiments, the fluid communicator may be relatively sterile. Further, the device may be used in association with a conventional infusion set, in which case the fluid communicator may be one or more parts of the infusion set, such as a standard Luer lock or other connector that is adapted to connect the device to the infusion set, or the fluid communicator may be omitted completely. In another embodiment, the pump patch is not limited to subcutaneous delivery. For example, the device may be connected to an indwelling infusion port, such as a central venous access port known in the art, in which case the fluid communicator may be a suitable adaptor for associating the device with the port.

In still another embodiment, the fluid communicator may comprise a microneedle array suitable for transdermal delivery of fluid drugs, as known in the art.

Although embodiments of the device are described above as comprising two separate portions that can be assembled together, or two separate portions and a needle insertion mechanism, in other embodiments the device may be a single portion or the device may have more than two separate portions.

Figure 7:
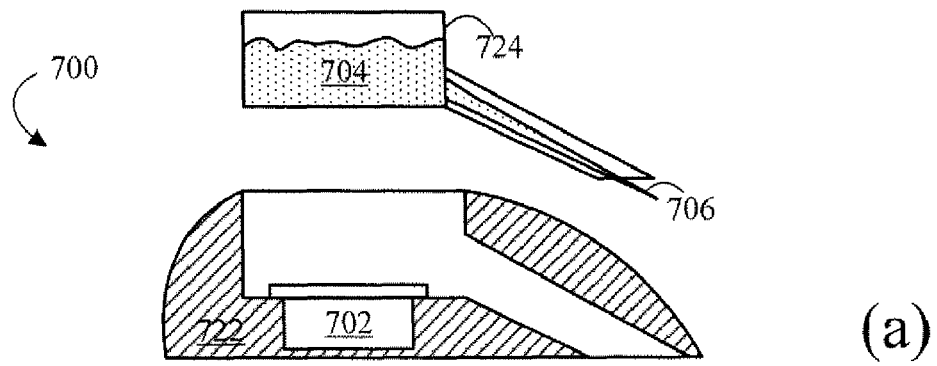
Figure 7:
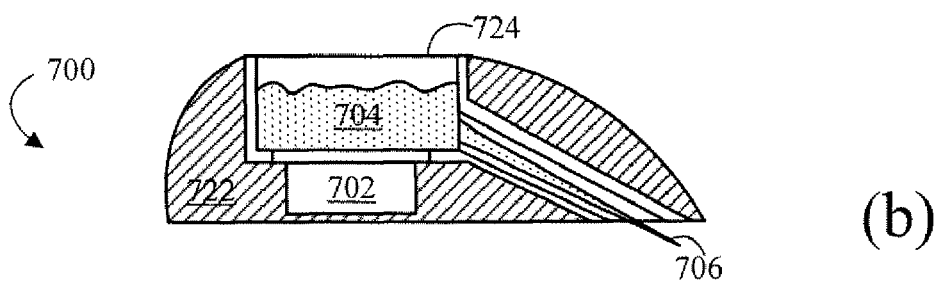
Figure 8:
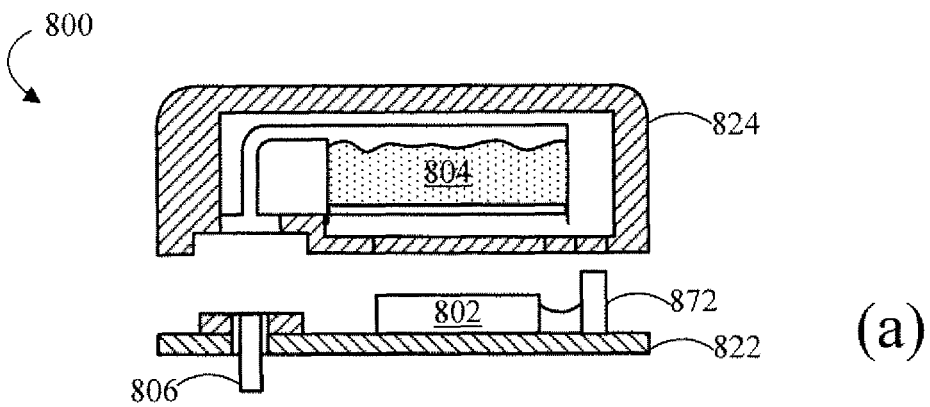
Figure 8:
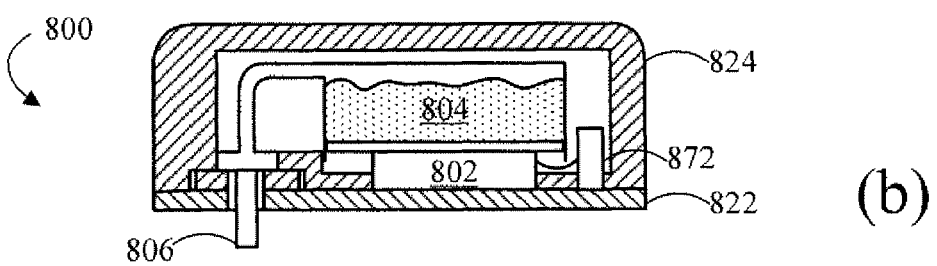

Further, in the embodiments described above, the fluid delivery system is generally housed in one portion of the device, namely, the movable portion. In other embodiments, the fluid delivery system may be housed in other portions of the device, such as the base portion, or in a combination of a number of portions of the device, such as a combination of the base portion and the movable portion. Examples are shown in FIGS. 7 and 8. FIG. 7, for example, illustrates an embodiment of a device 700 that is generally similar to the device 500. However, the fluid delivery system of the device 700 may be split between a base portion 722 and a movable portion 724. In an unassembled position, shown in FIG. 7(a), the base portion 722 may house an electrochemical actuator 702 while the movable portion 724 may house a fluid source 704 and a fluid communicator 706. In an assembled position, shown in FIG. 7(b), the electrochemical actuator 702 may be brought into direct or indirect communication with the fluid source 704.

FIG. 8 illustrates an embodiment of a device 800 that is generally similar to the device 600. However, the fluid delivery system of the device 800 may be split among a base portion 822 and a movable portion 824. In an unassembled position, shown in FIG. 8(a), the base portion 822 may house an electrochemical actuator 802 and a control system 872. The fluid communicator 806 may also be positioned in the base portion 822, after having been inserted via a needle insertion mechanism. The movable portion 824 may house a fluid source 804. In an assembled position, shown in FIG. 8(b), the electrochemical actuator 802 may be brought into direct or indirect communication with the fluid source 804.

Depending on the embodiment, the components of the fluid delivery system, including the electrochemical actuator, the fluid source, and the fluid communicator, may be positioned among various portions of the device, such as the base portion, the movable portion, and the needle insertion mechanism (if present). The components may be separated until the device is assembled to achieve selected design criteria, such as increased safety, decreased cost, or improved quality of life. For example, the wet and sterile components, such as the fluid source and fluid communicator, may be separated from the dry and non-sterile components, such as the electrochemical actuator and any associated electronics, for safety purposes. Examples of such embodiments include the device 700 and the device 800.

Some components may be separated to permit reusing one or more components while discarding one or more other components. Such embodiments may permit disposing of certain spent or damaged portions while reusing other fresh and functioning portions. For example, a fluid source that contains a relatively expensive drug may be separated from the electrochemical actuator and/or associated electronics to permit reusing the fluid source if the electrochemical actuator or electronics are defective. Alternatively, a fluid source that contains a drug delivered in relatively high volumes may be separated from the electrochemical actuator and associated electronics to permit reusing the electrochemical actuator and electronics with multiple fluid sources. As another example, electronics may be separated from the fluid source and/or electrochemical actuator to permit reusing the electronics even after the fluid source is empty and/or the electrochemical actuator has completely discharged. Further, the fluid communicator may be separated from one or more other components to permit reusing the other components in the event that needle insertion fails or the needle needs to be changed. An example of such an embodiment is the device 600, which includes the associated needle insertion mechanism. Further, some components may be separated to permit un-assembling and reassembling the device without reinserting the fluid communicator. Such an embodiment may permit certain activities, such as shopping and bathing. An example of such an embodiment is the device 600. Based on the above disclosure, a range of other configurations are possible. For example, the device may include a fluid communicator portion, an electrochemical actuator portion, a fluid source portion, and an electronics portions. These portions may be assembled to form a device of the type described herein, yet may be unassembled and reassembled to substitute and discard portions as necessary.

After the device is assembled, the electrochemical actuator may be activated so that the electrochemical actuator begins discharging, as further described below. The electrochemical actuator may actuate as it discharges, directly or indirectly acting on the fluid source to drive the fluid into the body. For example, the electrochemical actuator may be positioned in direct contact with the fluid source, such that actuation of the electrochemical actuator directly acts on the fluid source to deliver fluid out of the fluid source. Alternatively, a transferring structure or other appropriate mechanics may be positioned between the electrochemical actuator and the fluid source, such that actuation of the electrochemical actuator is transferred through the transferring structure to the fluid source. In embodiments, the transfer structure may amplify the change in volume or displacement experienced by the electrochemical actuator, such that a relatively small change in volume or displacement may produce the desired effect upon the fluid source.

For example, in the embodiment shown in FIG. 4, the electrochemical actuator 402 may directly act on the fluid source 404. As shown in FIG. 4(a), the fluid source 404 may be a deformable bladder or pouch positioned in direct contact with the electrochemical actuator 402. When the electrochemical actuator 402 actuates, a force or pressure may be applied to the fluid source 404, causing the fluid source 404 to deform, as shown in FIG. 4(b). The pressure within the fluid source 404 may increase, driving the fluid through the fluid communicator 406, as shown in FIG. 4(c).

In the embodiment shown in FIG. 6, the electrochemical actuator 602 may indirectly act on the fluid source 604 via, for example, a transfer structure 668. As shown in FIG. 6(c), the fluid source 604 may be a chamber, and the transfer structure 668 may be a piston in communication with the chamber. When the electrochemical actuator 602 actuates, a force may be applied to the transfer structure 668. In turn, the transfer structure 668 may apply a force to the fluid source 604 to drive fluid through the fluid communicator 606.

The transfer structure is described as a piston by way of example, although the transfer structure may have any other configuration envisioned by a person of ordinary skill based on the present disclosure. Such a transfer structure may comprise one or more known mechanical or electrical components arranged in any combination and/or location in the device that permits transferring work from the electrochemical actuator to the fluid source. Including a transfer structure may permit the device to have a range of different shapes, sizes and dimensions, as the electrochemical actuator need not be in direct physical contact with the fluid source.

By way of example, the fluid source is described above as being a bladder, reservoir, pouch, chamber or barrel. In other embodiments, the fluid source may be any component capable of retaining a fluid or drug in fluid form. In the illustrated embodiments, the fluid source may not be refillable, permitting disposal of the device. In other embodiments, the fluid source may be refilled, which may permit reusing at least a portion of the device and/or varying the drug or fluid delivered by the device.

In embodiments, the fluid source may be sized to correlate with the electrochemical potential of the electrochemical actuator. For example, the size and/or volume of the fluid source may be selected so that the fluid source becomes about substantially empty at about the same time that the electrochemical actuator becomes about substantially discharged. Such a configuration may permit reducing the size and/or cost of the device, as the fluid source may not be too large or contain too much drug in relation to the driving potential of the electrochemical actuator, and similarly, the electrochemical may not be too large or contain too much power in relation to the amount of drug in the fluid source. In other embodiments, the electrochemical actuator may be oversized with reference to the fluid source. Such a configuration may be used with relatively expensive drugs to ensure the fluid source is about substantially empty before the electrochemical actuator completely discharges, so that waste of the drug is reduced.

Further, the device may include more than one fluid source in some embodiments. Such a configuration may permit using a single device to deliver two or more drugs or fluids. The two or more drugs or fluids may be delivered discretely, simultaneously, alternating, according to a program or schedule, or in any other manner as further described below. In such embodiments, the fluid sources may be associated with the same or different electrochemical actuators, the same or different fluid communicators, the same or different operational electronics, or the same or different portions of the housing.

Figure 17:
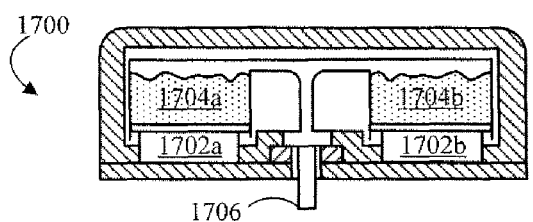
FIG. 17 is a side cross-sectional view of an embodiment of a pump device that includes multiple fluid sources operated by different electrochemical actuators.

One example embodiment is shown in FIG. 17, which is a side cross-sectional view of an embodiment of a pump device 1700 that includes multiple fluid sources 1704*a* and 1704*b*. The fluid sources 1704*a* and 1704*b* are operated by different electrochemical actuators 1702*a* and 1702*b*, respectively. The device 1700 may be suited for delivering two or more drugs or fluids in any configuration. For example, the device 1700 may be used in embodiments in which a drug is to be delivered at infrequent intervals over an extended period, such as a period of several days. In such an embodiment, one fluid source 1704*a* may comprise the drug and the other fluid source 1704*b* may comprise a fluid such as saline. The saline may be periodically administered between doses of the drug to impede clogs from forming in the fluid communicator 1706.

Figure 18:
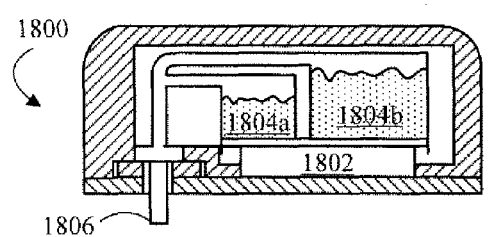
FIG. 18 is a side cross-sectional view of an embodiment of a pump device that includes multiple fluid sources operated by the same electrochemical actuator.

Another example embodiment is shown in FIG. 18, which is a side cross-sectional view of an embodiment of a pump device 1800 that includes multiple fluid sources 1802*a* and 1804*b* operated by the same electrochemical actuator 1802. The device 1800 may be suited for delivering two or more drugs or fluids in a range of configurations. For example, the device 1800 may be used in embodiments in which the drug or fluid has constituent components that are segregated prior to delivery into the body. For example, the drug may be stored in a dry powder form (e.g., lyophilized) in one compartment and then shortly or immediately prior to administration, it may be reconstituted into a solution or suspension with a suitable fluid vehicle known in the art, e.g., saline solution, for delivery. This may be particularly advantageous for certain drugs, such as biologics or protein drugs, that may preferably be in a lyophilized or other dry powder form in order to provide drug stability during storage, i.e., shelf stability. In these and in other embodiments, the fluid source 1802 may comprise a drug storage reservoir suited to store a drug or other non-fluid that can be reconstituted. In embodiments, intervening mechanics may transfer and/or amplify the displacement of the electrochemical actuator 1802 to each of the fluid sources 1804*a* and 1804*b* in different manners, permitting different fluid flow rates from the fluid sources 1804*b* and 1804*b*. Although devices having two fluid sources are illustrated, one of skill would understand that more than two fluid sources may be provided in other embodiments.

Devices having two or more fluid sources may have a number of different configurations within the scope and spirit of the present disclosure. For example, the fluid sources may be separated into different portions of the housing, which may permit replacing one of the fluid sources at a relatively higher frequency than the other fluid source. Further, the electrochemical actuator may be substituted with any other pump device, in which case one or more separate batteries may also be provided. The fluid sources may also have different sizes, shapes, and configurations depending on the use of the device.

It should be noted that the electrochemical actuator may be relatively small. For example, the electrochemical cell may have a volume in the range of about five cubic millimeters to about ten cubic centimeters, and more specifically in a range of about 0.1 cubic centimeters to about one cubic centimeter. The small size of the electrochemical actuator may permit reducing the size of the device. Further, the electrochemical actuator may include relatively few parts, reducing the size and cost of the device and increasing its reliability. The electrochemical actuator may power other components of the device. For example, the electrochemical actuator may power a display, a needle insertion mechanism, or other components of the device. Also, the electrochemical actuator may be relatively scalable, in a manner analogous to conventional batteries. For example, two or more electrochemical actuators may be provided, and in embodiments, the electrochemical actuator may be rechargeable. By way of example, the electrochemical actuator is described as driving, pumping, or expelling fluid from the fluid source. However, a person of skill would understand that the present disclosure encompasses other manners of delivering fluid from the fluid source. For example, the electrochemical actuator may pull fluid from the fluid source, such as by creating a vacuum within the fluid source, among other potential configurations. Further, the electrochemical actuator may be substituted with any known pump or other device suited to cause fluid flow from the fluid source, in which case a separate power source may also be provided.

The electrochemical actuator may be positioned in an electrical circuit within the device. The electrochemical actuator may comprise an electrochemical cell that is initially charged and actuates as it discharges. When the electrical circuit is open, the electrochemical actuator may be prevented from discharging, which may simultaneously prevent the electrochemical actuator from actuating. Thereby, fluid may be prevented from flowing out of the fluid source. When the electrical circuit is closed, the electrochemical actuator may begin discharging, simultaneously causing the electrochemical actuator to actuate. Thereby, fluid may be permitted to flow out of the fluid source. Thus, fluid may be expelled from the fluid source when the electrical circuit is closed but not otherwise.

In embodiments, the electrochemical actuator may discharge and actuate at rates that are dependent upon properties of the electrical circuit. When a proper of the electrical circuit is varied, the discharge rate of the electrochemical actuator may be varied, which may simultaneously vary the actuation of the electrochemical actuator. Thereby, the fluid flow rate out of the fluid source may be varied. In embodiments, the device may include means for controlling or regulating fluid flow from the device. The flow control means may be operative to vary properties associated with the electrical circuit, such as to start fluid flow from the device, stop fluid flow from the device, and/or vary a rate of fluid flow from the device. Embodiments of flow control means are described in detail below and can be implemented in any combination to permit delivering drugs according to one or more releases profiles. Release profiles that may be implemented may include release profiles having linear flow, non-linear flow, user-initiated flow, feedback responsive flow, or combinations of these flows, among others. For purposes of this disclosure, the term linear flow generally means flow that has a relatively constant flow rate. The term non-linear flow generally means flow that does not necessarily have a relatively constant flow rate, including modulated flow, pulsatile flow, discontinuous flow, and/or flow that correlates to a program or schedule that may not necessarily require a relatively constant flow rate. The term user-initiated flow generally means flow that is initiated in response to an input into the device. The term feedback-responsive flow generally means flow that adjusts in response to one or more sensed conditions, described below. Thus, the pump device may be effective to deliver a wider variety of drug therapies than other pump devices.

Figure 9:
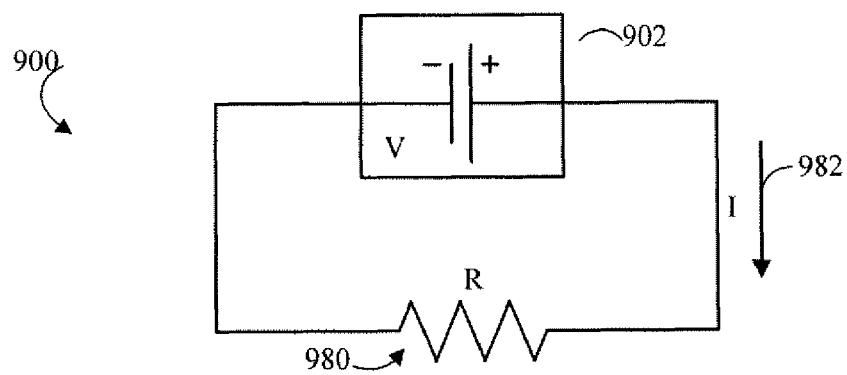
FIG. 9 is a schematic illustrating an embodiment of an electrical circuit that may be used in an embodiment of a pump device.

FIG. 9 is a schematic illustrating an embodiment of an electrical circuit 900 that may be used to power embodiments of a pump device. As shown, the electrical circuit 900 may include an electrochemical actuator 902 positioned in electrical communication with a resistor 980. The electrochemical actuator 902 may comprise an electrochemical cell that is initially charged at a relatively constant voltage, and displaces as it discharges. The resistor 980 may have a relatively constant electrical resistance. When the electrical circuit 900 is closed, as shown, a current 982 may be induced in the electrical circuit 900. The electrochemical actuator 902 may begin discharging across the resistor 980, simultaneously causing the electrochemical actuator 902 to actuate. Thereby, fluid may be permitted to flow out of the fluid source.

More specifically, the discharge of the electrochemical actuator 902 may be relatively proportional to the current 982 traveling through the electrical circuit 900, or stated alternatively, the electrical resistance of the resistor 980. Because the electrical resistance of the resistor 980 may be relatively constant, the electrochemical actuator 902 may discharge at a relatively constant rate. Thus, the discharge of the electrochemical actuator 902 may be relatively linear with the passage of time, meaning the displacement of the electrochemical actuator 902 may be relatively linear with the passage of time.

Figure 10:
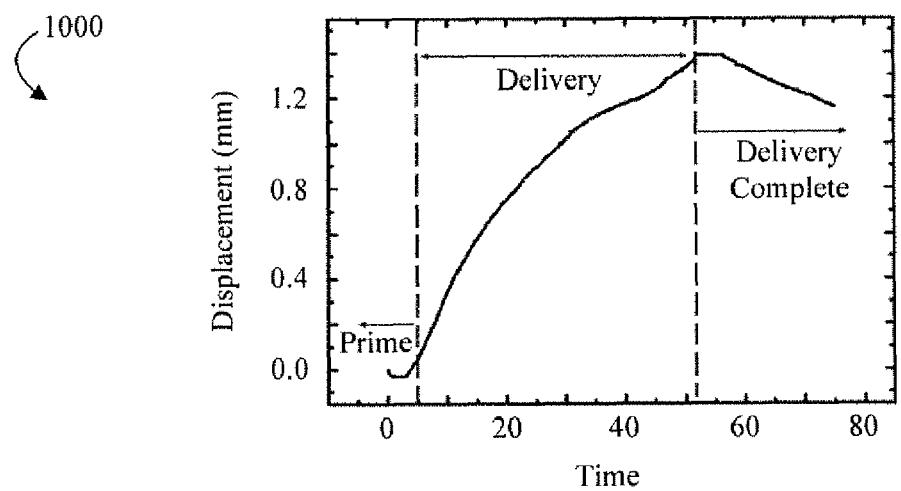
FIG. 10 is a graph illustrating one exemplary, non-limiting embodiment of a displacement curve, indicating the displacement behavior as a function of time for an electrochemical actuator positioned in the electrical circuit of FIG. 9.

FIG. 10 is a graph illustrating an embodiment of a displacement curve 1000, indicating the displacement behavior as a function of time for the electrochemical actuator 902 positioned in the electrical circuit 900 of FIG. 9. As shown, the displacement of the electrochemical actuator 902 is relatively linear with the passage of time under the conditions described above. In embodiments, the electrochemical actuator 902 may linearly displace for a time period that ranges from several minutes to several days. For example, the electrochemical actuator 902 may linearly displace for a time period in the range of about five minutes to about five weeks, and more specifically in a range of about five hours to about five days. Thereafter, the linear displacement may taper off and become non-linear, as the electrochemical cell reaches a completely discharged state and the electrochemical actuator 902 stops actuating.

Figure 11:
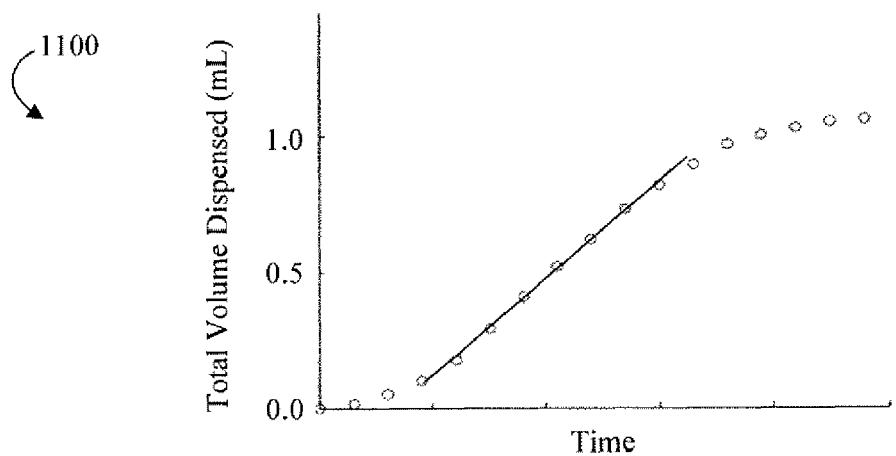
FIG. 11 is a graph illustrating one exemplary, non-limiting embodiment of a fluid flow curve, indicating the fluid flow behavior as a function of time for a fluid source associated with the electrical circuit of FIG. 9.

FIG. 11 is a graph illustrating an embodiment of a fluid flow curve 1100, indicating the fluid flow behavior as a function of time for a fluid source associated with the electrical circuit 900 of FIG. 9. Because the displacement rate of the electrochemical actuator 902 is relatively constant as shown in FIG. 10, the fluid flow rate from the device also may be relatively constant, as shown in FIG. 11. Thus, a device comprising the electrical circuit 900 may deliver fluid according to a relatively continuous release profile, meaning the fluid may flow at a relatively constant rate until the fluid source becomes empty or the electrochemical actuator becomes completely discharged.

In embodiments, the device may experience a brief priming period at start-up during which the fluid flow rate may not be relatively constant. For example, the displacement curve 1000 demonstrates that the electrochemical actuator 902 may experience a brief priming period when the electrochemical actuator 902 is first discharged. During the priming period, reaction products may not have accumulated on the electrochemical actuator 902, preventing the electrochemical actuator 902 from displacing linearly. To compensate for such a priming period, the electrochemical actuator 902 may be briefly discharged prior to use, so that when the device is in use, the electrochemical actuator 902 may experience relatively linear displacement almost immediately. Further, the fluid flow curve 1100 indicates the fluid source may experience a brief priming period when the electrochemical actuator 902 first displaces. During the priming period, the fluid source may be pressurized and fluid may begin traveling toward the fluid communicator. To compensate for such a priming period, the fluid source may initially be pressurized, and a check valve may be provided adjacent to the fluid communicator, such that fluid begins flowing through the fluid communicator almost immediately after the electrochemical actuator begins displacing. For example, the fluid source 604 is not pressurized in the device 600 shown in FIG. 6(d), and therefore fluid may not initially flow from the device 600 at a relatively constant rate, but such issue may be addressed by pressurizing the fluid source 604 and providing the check valve adjacent to the fluid communicator 606.

Because the displacement of the electrochemical actuator may be relatively proportional to the current passing through the electrical circuit, the electrochemical actuator may be relatively easy to control. For example, the displacement of the electrochemical actuator may be varied by one or more flow control means positioned in the electrical circuit. Examples of such flow control means include one or more electrical contacts, switches, controllers, circuitry components, or combinations thereof, as further described below. The flow control means may be operative to control the electrical circuit. For example, the flow control means may be operative to open or close the electrical circuit. When the flow control means open the electrical circuit, the electrochemical actuator may stop discharging and actuating, such that the fluid is not expelled from the fluid source. When the flow control means closes the electrical circuit, the electrochemical actuator may begin discharging and actuating, such that fluid is expelled from the fluid source. The flow control means also may be operative to vary the current through the electrical circuit, such as by varying the resistance of the electrical circuit. When the flow control means varies the current or the resistance, the electrochemical actuator may discharge at a varied rate, such that the electrochemical actuator displaces at a varied rate to expel from the fluid source at a varied flow rate.

Figure 12:
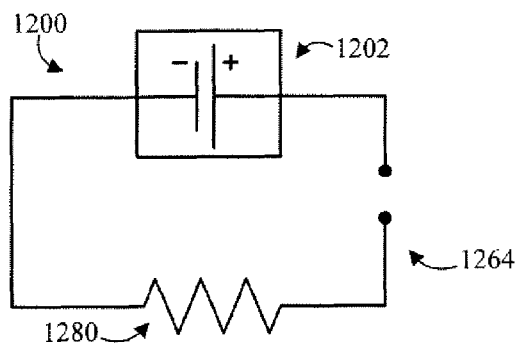
FIG. 12 is a schematic illustrating an embodiment of an electrical circuit that includes electrical contacts.

FIG. 12 is a schematic illustrating an embodiment of an electrical circuit 1200 that includes electrical contacts 1264. The electrical contacts 1264 may permit the electrochemical actuator 1202 to displace when the electrical contacts 1264 are in electrical communication with each other, but not otherwise. As shown, the electrical contacts 1264 are not in electrical communication with each other. Therefore, the electrical circuit 1200 is broken. The electrochemical actuator 1202 is not discharging or displacing, and therefore fluid is not flowing. In embodiments, such electrical contacts 1264 may preserve the electrochemical actuator 1202 in the charged state until the device is assembled, so that the electrochemical cell may not lose charge until the device is to be used. Such electrical contacts 1264 may also prevent fluid flow until the device is assembled.

Such an embodiment is shown and described with reference back to FIG. 4. Specifically, electrical contacts 464 may be positioned in the base portion 422 and the movable portion 424. The electrical contacts 464 are shown as (+) and (−) for illustrative purposes, although the configuration may be reversed in other embodiments. When the device 400 is in the unassembled position shown in FIG. 4(a), the electrical contacts 464 may not contact each other, breaking the electrical circuit to prevent the electrochemical actuator 402 from discharging and actuating. When the device 400 is moved into the assembled position shown in FIG. 4(b), the electrical contacts 464 may contact each other to close the electrical circuit, permitting the electrochemical actuator 402 to begin discharging and actuating, provided the electrical circuit is not broken in some other place. Subsequently, the electrochemical actuator 402 may act on the fluid reservoir 404 to deliver fluid out of the fluid communicator 406, as shown in FIG. 4(c). It should be noted that assembling the device 400 may not cause the electrical contacts 464 to directly contact each other, but instead may place the electrical contacts 464 in electrical communication with each other so that the electrical circuit can be closed. Alternatively, the electrical contacts may be omitted completely, in which case the electrochemical actuator may or may not be prevented from discharging when the device is unassembled.

With reference back to FIG. 12, when the electrical contacts 1264 are positioned in the electrical circuit 1200 with an electrochemical actuator 1202 having a relatively constant voltage and a resistor 1280 having a relatively constant electrical resistance, fluid may not be delivered until the device is assembled, and thereafter fluid may be delivered according to a relatively continuous release profile. Specifically, fluid may begin flowing once the device is assembled and may continue flowing at a relatively constant rate until the electrochemical actuator becomes completely discharged or the fluid source becomes empty. Alternatively, the release profile may be varied by implementing one or more additional flow control means as further described below.

Figure 13:
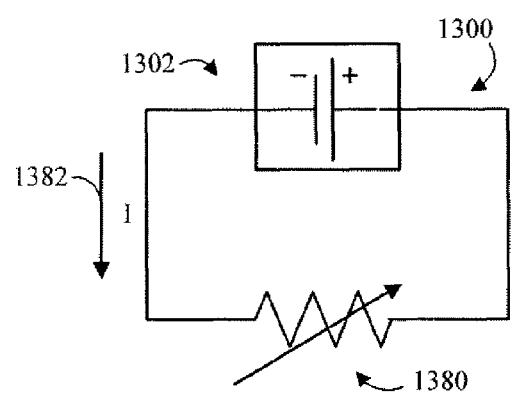
FIG. 13 is a schematic illustrating an embodiment of an electrical circuit that includes a variable resistor.

FIG. 13 is a schematic illustrating an embodiment of an electrical circuit 1300 that includes a variable resistor 1380. The variable resistor 1380 may be any electrical component having an electrical resistance that may be altered or controlled. More specifically, varying the variable resistor 1380 may vary the current 1382 induced in the circuit 1300, which in turn may vary the discharge rate of the electrochemical actuator 1302. Similarly, varying the discharge rate of the electrochemical actuator 1302 may vary the displacement rate of the electrochemical actuator 1302, which in turn may vary the fluid flow rate from the fluid source. Thus, the electrical resistance of the variable resistor 1380 may be adjusted to control the fluid flow from the fluid source. The adjustment in the fluid flow may be proportional to the adjustment in the electrical resistance, due to the principles described above.

Figure 14:
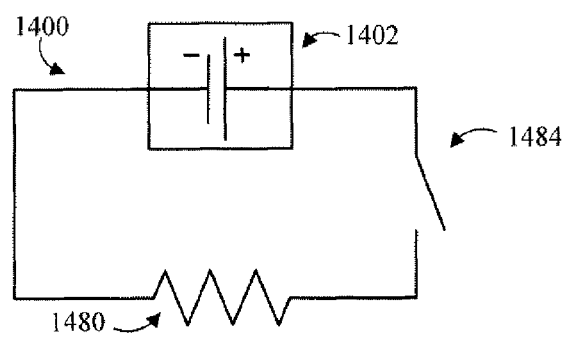
FIG. 14 is a schematic illustrating an embodiment of an electrical circuit that includes a switch.

FIG. 14 is a schematic illustrating an embodiment of an electrical circuit 1400 that includes a switch 1484. The switch 1484 may be operative to open or close the electrical circuit 1400. When the switch 1484 is closed, the electrochemical actuator 1402 may discharge. For example, the electrochemical actuator 1402 may discharge at a relatively constant rate in embodiments in which the resistor 1480 has a relatively constant electrical resistance. When the switch 1484 is opened, the electrochemical actuator 1402 may be prevented from discharging, which prevents the electrochemical actuator 1402 from displacing. Thus, the switch 1484 may be adjusted to control the fluid flow from the fluid source.

Figure 15:
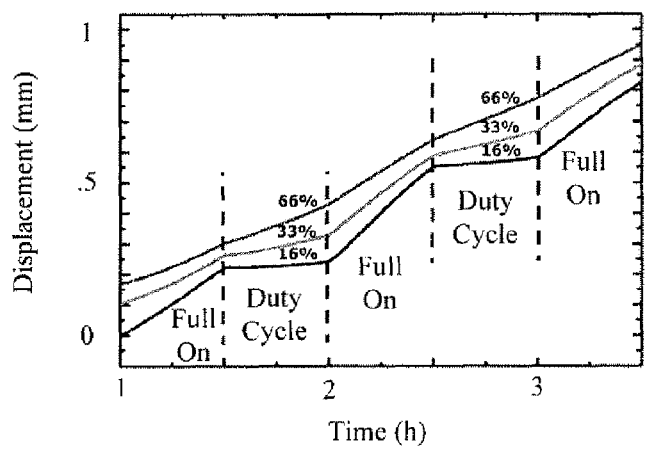
FIG. 15 is a graph illustrating a displacement curve, indicating the displacement behavior as a function of time for a fluid source associated with the electrical circuit of FIG. 14.

FIG. 15 is a graph illustrating a displacement curve 1500, indicating the displacement behavior as a function of time for a fluid source associated with the electrical circuit 1400 of FIG. 14. The switch 1484 may be intermittently opened and closed to vary the duty cycle of the electrochemical actuator 1402, thereby varying the displacement of the electrochemical actuator 1402. For example, during a full on cycle, the switch 1484 may be closed so that the electrochemical actuator 1402 may displace at a relatively constant rate. During a duty cycle, the switch 1484 may be intermittently opened and closed so that the effective displacement rate of the electrochemical actuator 1402 is relatively lower than the displacement rate during the full on cycle. Specifically, the effective displacement rate may depend upon the amount of time the switch 1484 spends in the opened and closed positions. The displacement curve 1500 illustrates the displacement for the electrochemical actuator 1402 when the switch 1484 is closed during the duty cycle for 16% of the time, 33% of the time, and 66% of the time, respectively, although any configuration is possible. As shown, closing the switch 1484 for 66% of the time results in a relatively higher effective displacement rate, and therefore a relatively higher fluid flow rate, than closing the switch 1484 for 33% of the time or 16% of the time.

Figure 16:
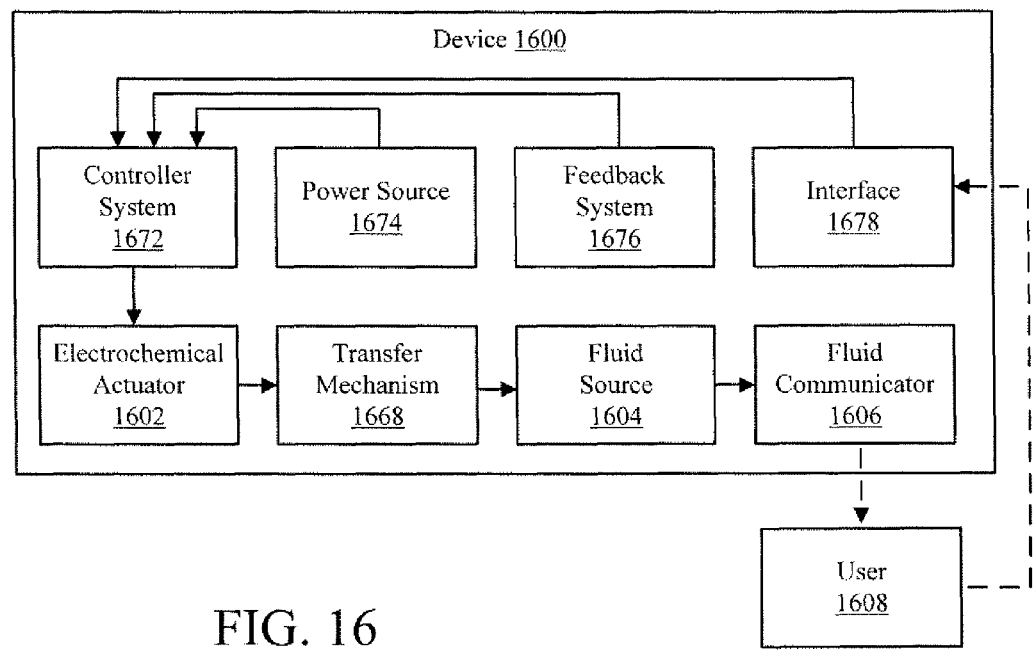
FIG. 16 is a schematic view of an embodiment of a device that includes an embodiment of a control system.

FIG. 16 is a schematic view of an embodiment of a device 1600 that includes an embodiment of a control system 1672. The control system 1672 may be adapted to control an electrochemical actuator 1602. Specifically, the control system 1672 may vary the displacement of the electrochemical actuator 1602 to vary the fluid flow rate from a fluid source 1604, through a fluid communicator 1606, and into a user 1608. For example, the control system 1672 may vary the displacement of the electrochemical actuator 1602 by opening the circuit, closing the circuit, or varying the current or resistance of the circuit. Thereby, the control system 1672 may permit administering a selected release profile or altering a release profile. For example, the control system 1672 may administer a constant fluid flow rate, a varied fluid flow rate, a continuous fluid flow, a discontinuous fluid flow, a modulated fluid flow, a pulsed fluid flow, a programmed fluid flow, a scheduled fluid flow, a feedback responsive fluid flow, a user-controlled fluid flow, or a fluid flow that is varied at a rate responsive to a biological or mechanical measure. Therefore, the control system 1672 may permit safe delivery of the drug therapy in a manner that benefits the user 1608.

The control system 1672 may comprise one or more flow control means, such as one or more of the electrical contacts, resistor, variable resistor, and switch described above, or other known circuitry components or combinations thereof. In embodiments, the control system 1672 may also comprise a controller and a memory, such as a microcontroller or a state machine. The memory may include a program of operation comprising a set of instructions executable by the controller. The controller may execute the program of operation to vary the current or resistance of the electrical circuit according to the set of instructions. For example, the controller may be operative to control the one or more flow control means to open the circuit, close the circuit, or vary the current or resistance of the circuit. Thereby, the controller may be operative to vary the fluid flow from the device to achieve a selected release profile. For example, the release profile may be a programmed release profile, a scheduled release profile, or a release profile that is response to one more inputs received from, for example, a feedback system 1676 or a user interface 1678. In embodiments, the control system 1672 may be powered by an external power source 1674. The power source 1674 may be another electrochemical actuator of suitable voltage, although the power source 1674 may have any other configuration or may be omitted.

In other embodiments, the flow control means may be arranged within the electrical circuit to control the circuit in a particular manner as a function of time, in which case control system 1672 may not include the controller and in which case a pre-defined release profile may be "hard-coded" into the electrical circuit.

In embodiments, the control system 1672 may control the electrical circuit according to the time of day. For example, a schedule may be set by the user. Such an embodiment may permitting controlling the flow according to the circadian rhythm of the body.

In embodiments, the control system 1672 may permit controlling the electrical circuit in response to inputs received from one or both of the feedback system 1676 and the user interface 1678. For example, the control system 1672 may open the circuit, close the circuit, or vary the current or resistance of the circuit in response to the inputs.

The feedback system 1676 may be adapted to measure or otherwise sense one or more conditions associated with the device and/or the user. For example, the feedback system 1676 may sense an actual current through the electrical circuit, an actual voltage across the electrical circuit, an actual discharge of the electrochemical actuator 1602, an actual displacement of the electrochemical actuator 1602, an actual fluid flow out of the fluid source 1604, an actual fluid flow through the fluid communicator 1606, an actual current rate through the electrical circuit, an actual voltage rate across the electrical circuit, an actual discharge rate of the electrochemical actuator 1602, an actual displacement rate of the electrochemical actuator 1602, an actual fluid flow rate out of the fluid source 1604, an actual fluid flow rate through the fluid communicator 1606, proxies for these conditions, other conditions, or combinations thereof. For example, the feedback system 1676 may comprise one or more sensors known in the art and appropriately positioned within the device 1600, such as a strain gauge, a capacitive sensor, a variable resistance sensor, a flow sensor, or a vision sensor, among others. The feedback system 1676 may provide the sensed conditions to the control system 1676, which may be operative to change the discharge rate of the electrochemical actuator 1602 in response to the sensed conditions, such as by opening the circuit, closing the circuit, or varying the current or resistance of the circuit. Thereby, the control system 1676 may maintain the desired release profile.

In embodiments, the feedback system 1676 may be in communication with the user and may sense one or more conditions associated with the user. For example, the feedback system 1676 may remove a bodily fluid from the user 1608, and in response the control system 1672 may adjust the release profile. The feedback system 1676 may also be in communication with a power source, such as the power source 1674, which may be another electrochemical actuator. In another variation, the feedback system 1676 may include a biosensor, e.g., to assess the concentration of one or more analytes in a physiological fluid of the patient.

As mentioned above, the control system 1672 may be in communication with a user interface 1608. The user interface 1678 may accept one or more inputs from the user, and the control system 1672 may adjust the release profile in response to the input. The user inputs may comprise one or more of the following: a request to initiate fluid flow, a request to discontinue fluid flow, a request to cause temporarily fluid flow, and a request to vary the fluid flow rate. For example, the device may include one or more user-responsive controls such as a switch, a button, or a slider. The switch may permit the user to turn the fluid flow on or off, such as by opening or closing the circuit. The button may permit the user to initiate a temporary fluid flow, such as by temporarily closing the circuit. The slider may permit the user to vary the flow rate of the fluid flow, such as by varying the current through the electrical circuit. The user interface 1608 may also include a display, which may display information delivered by the control system 1672, such as the number of doses dispensed and/or a number of doses remaining. Such information may be provided to the control system 1672 by, for example, the feedback system 1676.

Thus, the control system 1672 may permit delivering drugs continuously, on-demand, or in a modulated manner. The device may be used, for example, for continuous delivery of normally injected compounds, for the delivery of compounds requiring titration and precise control, or for on-demand patient controlled analgesia.

The device 1600 is shown and described by way of example, and other configurations are included within the scope of the present disclosure. For example, the displacement of the electrochemical actuator 1602 may be transferred to the fluid source 1604 through a transfer mechanism 1668 as shown, although the transfer mechanism 1668 may be omitted. Further, the feedback system 1676 and/or the user interface 1678 may be omitted, in which case the control system 1676 may not be responsive to feedback or inputs received from the user 1608, respectively.

By way of example, the flow control means are described above as controlling the fluid flow from the device by controlling the discharge of the electrochemical actuator. Such embodiments may preserve the potential of the electrochemical actuator, such that discharge of the electrochemical actuator results in correlated fluid flow. In other embodiments, the electrochemical actuator may actuate as it charges, in which case charging the electrochemical actuator results in correlated fluid flow. In still other embodiments, the flow control means may control the fluid flow by controlling the transfer structure or other intervening mechanics between the electrochemical actuator and the fluid source. In such embodiments, the electrochemical actuator may continuously discharge, but transfer of the correlated displacement may be interrupted or reduced in amplification by the transfer mechanism. A person of skill may be able to implement such a configuration based on the above disclosure.

Upon reading the present disclosure, a person of skill would appreciate that the described embodiments of the device are merely illustrative examples that convey the scope and breadth of the present disclosure. Other embodiments of the device that combine portions of the embodiments described above are included within the scope of the present disclosure.

Embodiments of the present device may be used to deliver a variety of drugs according to one or more release profiles. For example, the drug may be delivered according to a relatively uniform flow rate, a varied flow rate, a preprogrammed flow rate, a modulated flow rate, in response to conditions sensed by the device, in response to a request or other input from a user or other external source, or combinations thereof. Thus, embodiments of the present device may be used to deliver drugs having a short half-life, drugs having a narrow therapeutic window, drugs delivered via on-demand dosing, normally-injected compounds for which other delivery modes such as continuous delivery are desired, drugs requiring titration and precise control, and drugs whose therapeutic effectiveness is improved through modulation delivery or delivery at a non-uniform flow rate. These drugs may already have appropriate existing injectable formulations.

For example, the present devices may be useful in a wide variety of therapies. Representative examples include, but are not limited to, insulin delivery for Type 1 or Type 2 diabetes; leutenizing hormone releasing hormone (LHRH) or follicle stimulating hormone (FSH) for infertility; immunoglobulin for autoimmune diseases; apomorphine for Parkinson's disease; interferon A for chronic hepatitis B, chronic hepatitis C, solid or hematologic malignancies; antibodies for the treatment of cancer; octreotide for acromegaly; ketamine for pain, refractory depression, or neuropathic pain; heparin for post-surgical blood thinning; corticosteroid (e.g., prednisone, hydrocortisone, dexamethasone) for treatment of MS; morphine, hydromorphone, fentanyl or other opioids or non-opioids for post-operative pain or for chronic and breakthrough pain; and tizanidine for spasticity (e.g., MS. SCI, etc.).

In a particular embodiment, the device may be used to administer ketamine for the treatment of refractory depression or other mood disorders. In embodiments, ketamine may include either the racemate, single enantiomer (R/S), or the metabolite (wherein S-norketamine may be active).

In another particular embodiment, an embodiment of the device herein may be used for administration of Interferon A for the treatment of hepatitis C. In one embodiment, a several hour infusion patch is worn during the day or overnight three times per week, or a continuous delivery system is worn 24 hours per day. Such a device may advantageously may replace bolus injection with a slow infusion, reducing side effects and allowing the patient to tolerate higher doses. In other Interferon A therapies, the device may also be used in the treatment of malignant melanoma, renal cell carcinoma, hairy cell leukemia, chronic hepatitis B, condylomata acuminata, follicular (non-Hodgkin's lymphoma, and AIDS-related Kaposi's sarcoma.

In still another particular embodiment, an embodiment of the device described herein may be used for administration of apomorphine or other dopamine agonists in the treatment of Parkinson's Disease ("PD"). Currently, a bolus subcutaneous injection of apomorphine may be used to quickly jolt a PD patient out of an "off" state. However, apomorphine has a relatively short half-life and relatively severe side effects, limiting its use. The device described herein may provide continuous delivery and may dramatically reduce side effects associated with both apomorphine and dopamine fluctuation. In one particular embodiment, the device provides continuous delivery of apomorphine or other dopamine agonist, with, optionally, an adjustable baseline and/or a bolus button for treating an "off" state in the patient. Advantageously, this method of treatment may provide improved dopaminergic levels in the body, such as fewer dyskinetic events, fewer "off" states, less total time in "off" states, less cycling between "on" and "off" states, and reduced need for levodopa; quick recovery from "off" state if it occurs; and reduced or eliminated nausea/vomiting side effect of apomorphine, resulting from slow steady infusion rather than bolus dosing.

In yet another embodiment, an embodiment of the device may be used for administration of an analgesic, such as morphine, hydromorphone, fentanyl or other opioids, in the treatment of pain. Advantageously, the device may provide improved comfort in a less cumbersome and/or less invasive technique, such as for post-operative pain management. Particularly, the device may be configured for patient-controlled analgesia.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A patch pump device comprising:
    at least one fluid source;
    a fluid communicator in fluid communication with the at least one fluid source;
    an insertion mechanism configured to insert the fluid communicator into the body of a patient, the insertion mechanism including a spring coupled to the fluid communicator, and a latch configured to restrain the spring in a compressed state; and
    an electrochemical actuator including an electrode configured to deflect as the electrochemical actuator discharges, the deflection of the electrode being operative to cause fluid to be delivered from the at least one fluid source into the fluid communicator.

2. The patch pump device of claim 1, wherein:
    the at least one fluid source comprises a deformable bladder, and
    the electrochemical actuator is in direct contact with the deformable bladder.

3. The patch pump device of claim 1, further comprising a transfer structure positioned between the at least one fluid source and the electrochemical actuator, the transfer structure being adapted to transfer mechanical work produced by the electrochemical actuator to the at least one fluid source.

4. The patch pump device of claim 3, wherein:
    the at least one fluid source comprises a chamber or barrel, and
    the transfer structure comprises a piston.

5. The patch pump device of claim 1, further comprising control means operative to regulate fluid flow from the device.

6. The pump patch device of claim 1, further comprising control means operative to implement a release profile of fluid from the at least one fluid source that includes one or more of the following fluid flows: a linear flow, a non-linear flow, a continuous flow, a discontinuous flow, a programmed flow, a user-initiated flow, and a feedback responsive flow.

7. The pump patch device of claim 1, further comprising control means operative to regulate fluid flow from the device in response to one or more sensed conditions.

8. The pump patch device of claim 7, wherein the sensed conditions comprise one or more of the following: a current applied through the electrochemical actuator, a voltage applied across the electrochemical actuator, the discharge of the electrochemical actuator, a displacement of the electrochemical actuator, a fluid flow out of the fluid source, a fluid flow through the fluid communicator, a current rate applied through the electrochemical actuator, a voltage rate applied across the electrochemical actuator, a discharge rate of the electrochemical actuator, a displacement rate of the electrochemical actuator, a fluid flow rate out of the fluid source, and a fluid flow rate through the fluid communicator.

9. The pump patch device of claim 1, further comprising control means operative to regulate fluid flow from the device in response to one or more user inputs.

10. The pump patch device of claim 9, wherein the one or more user inputs comprise one or more of the following: a request to initiate fluid flow, a request to discontinue fluid flow, a request to cause temporary fluid flow, and a request to vary the fluid flow rate.

11. The patch pump device of claim 1, wherein:
the electrochemical actuator is positioned in an electrical circuit, and
the patch pump device further comprises control means operative to perform one or more of the following: open the electrical circuit, close the electrical circuit, vary the current through the electrical circuit, and vary the resistance of the electrical circuit.

12. The patch pump device of claim 1, wherein:
the electrochemical actuator experiences a displacement that is relatively proportional to a current though an electrical circuit, and
a fluid flow rate out of the device is relatively proportional to a displacement rate of the electrochemical actuator.

13. The patch pump device of claim 12, further comprising control means operative to vary the displacement rate of the electrochemical actuator to vary the fluid flow rate out of the device.

14. The patch pump device of claim 1, further comprising a second fluid source.

15. The patch pump device of claim 14, wherein the fluid communicator is operative to be in fluid communication with the second fluid source and the electrochemical actuator is operative to cause fluid to be delivered from the second fluid source into the fluid communicator.

16. The patch pump device of claim 14, further comprising a second electrochemical actuator, wherein the fluid communicator is operative to be in fluid communication with the second fluid source and the second electrochemical actuator is operative to cause fluid to be delivered from the second fluid source into the fluid communicator.

17. The patch pump device of claim 15, wherein the at least one fluid source comprises a first drug, and the second fluid source comprises a second drug.

18. The patch pump device of claim 16, wherein the at least one fluid source comprises a first drug, and the second fluid source comprises a second drug.

19. The patch pump device of claim 18, which is operative to deliver the first and second drugs simultaneously.

20. The patch pump device of claim 18, which is operative to deliver the first and second drugs sequentially.

21. The patch pump device of claim 15, wherein the at least one fluid source comprises a drug, and the second fluid source comprises saline without a drug.

22. The patch pump device of claim 21, which is operative to deliver the drug intermittently and to deliver the saline without the drug at one or more times when the drug is not being delivered.

23. The patch pump device of claim 16, wherein the at least one fluid source comprises a drug, and the second fluid source comprises saline without a drug.

24. The patch pump device of claim 23, which is operative to deliver the drug intermittently and to deliver the saline without the drug at one or more times when the drug is not being delivered.

25. The patch pump device of claim 1, wherein the at least one fluid source comprises a fluid comprising at least one drug.

26. The patch pump device of claim 1, further comprising a drug storage reservoir comprising a drug, wherein the at least one fluid source is operative to be in fluid communication with the drug storage reservoir to reconstitute the drug in the fluid for delivery into the fluid communicator.

27. The patch pump device of claim 26, wherein the drug in the drug storage reservoir is in a lyophilized or other dry powder form.

28. A device for delivering fluid to the body of a patient, comprising:
at least one fluid source;
a cannula in fluid communication with the at least one fluid source;
a housing suited for removably associating the fluid source and the cannula with the body of the patient, the housing including a base portion and a movable portion and being movable between an unassembled position and an assembled position by moving the movable portion with reference to the base portion;
an insertion mechanism, the insertion mechanism operable to cause the cannula to move with respect to the housing and to insert the cannula into the body of the patient; and
an electrochemical actuator operative to cause fluid to be delivered from the at least one fluid source into the cannula.

29. The device of claim 28, wherein:
the electrochemical actuator comprises a charged electrochemical cell, and
at least a portion of the electrochemical cell experiences a change in volume or position in response to an applied current.

30. The device of claim 28, wherein the at least one fluid source comprises a fluid drug formulation.

31. The device of claim 28, wherein the insertion mechanism is adapted for removable association with at least a portion of the housing.

32. The device of claim 28, wherein the housing comprises an adhesive for removably associating the device with the human body.

33. The device of claim 28, wherein when the housing is in the assembled position, the housing takes on an outer shape that is relatively smooth and free from sharp edges.

34. The device of claim 28, wherein when the housing is in the assembled position, the base portion and the movable portion releasably lock together.

35. The device of claim 28, wherein the electrochemical actuator is activated by moving the housing between the unassembled position and the assembled position.

36. The device of claim 28, wherein:
the base portion comprises a first electrical contact,
the movable portion comprises a second electrical contact, and
the first and second electrical contacts arc positioned to contact each other when the housing is in the assembled position but not when the housing is in the unassembled position.

37. The device of claim 28, wherein the cannula is associated with the housing such that the cannula is retracted inside the housing when the housing is in the unassembled position and the cannula is transferred outside of the housing when the housing is in the assembled position.

38. The device of claim 28, wherein the cannula is inserted by moving the housing from the unassembled position to the assembled position.

39. The device of claim 28, further comprising a control system operative to regulate fluid flow from the device.

40. The device of claim 39, further comprising a feedback system in communication with the control system.

41. The device of claim 39, further comprising a user interface in communication with the control system.

42. The patch pump device of claim 1, wherein the fluid source includes a drug selected from the group consisting of insulin, leutenizing hormone releasing hormone, follicle stimulating hormone, immunoglobulin, apomorphine, interferon A, octreotide, ketamine, heparin, corticosteroids, opioids, non-opioid analgesics; tizanidine, and combinations thereof.

43. The device of claim 30, wherein the a fluid drug formulation includes a drug selected from the group consisting of insulin, leutenizing hormone releasing hormone, follicle stimulating hormone, immunoglobulin, apomorphine, interferon A, octreotide, ketamine, heparin, corticosteroids, opioids, non-opioid analgesics; tizanidine, and combinations thereof.

44. The patch pump device of claim 1, wherein the spring transitions from the compressed state to an uncompressed state when the latch is released, thereby inserting the fluid communicator into the body of a patient.

45. The patch pump device of claim 1, wherein the insertion mechanism includes a needle slidably disposed within the fluid communicator.

46. The device of claim 28, wherein the electrochemical actuator includes an electrode configured to deflect as the electrochemical actuator discharges thereby causing fluid to be delivered from the at least one fluid source into the cannula.

47. The device of claim 28, wherein the insertion mechanism includes a spring coupled to the cannula, and a latch configured to restrain the spring in a compressed state.

48. The device of claim 47, wherein the spring transitions from the compressed state to an uncompressed state when the latch is released, thereby inserting the cannula into the body of a patient.

49. A device for delivering fluid to the body of a patient, comprising:
a fluid delivery system including a fluid source, a cannula, and an electrochemical actuator having a bimorph electrode and configured to change volume or position as the bimorph electrode discharges; and
a housing configured for removably associating the fluid delivery system with the body of the patient, the housing being movable between an unassembled configuration in which the fluid delivery system is in a deactivated state, and an assembled configuration in which a first portion forms a cooperative fit with a second portion, the first portion of the housing includes a first electrical contact and the second portion of the housing includes a second electrical contact, the first and second electrical contacts being positioned to contact each other when the housing is in the assembled position to activate the electrochemical actuator thereby delivering fluid from the fluid source through the cannula.

50. The device of claim 49, wherein the cannula is in fluidically isolated from the fluid source in the unassembled configuration.

51. The device of claim 49, wherein the cannula is movable from a retracted position in which the cannula is disposed inside the housing when the housing is in the unassembled configuration and a deployed position in which the cannula protrudes outside the housing when the housing is in the assembled configuration.

52. The device of claim 49, further comprising:
an insertion mechanism, the insertion mechanism configured to insert the cannula into the body of the patient when the housing is moved between an unassembled configuration and the assembled configuration.

* * * * *